US006825921B1

(12) United States Patent
Modlin et al.

(10) Patent No.: US 6,825,921 B1
(45) Date of Patent: Nov. 30, 2004

(54) MULTI-MODE LIGHT DETECTION SYSTEM

(75) Inventors: Douglas N. Modlin, Palo Alto, CA (US); John C. Owicki, Palo Alto, CA (US); Jon F. Petersen, Redwood City, CA (US); Todd E. French, Cupertino, CA (US); Carl L. Wright, Kilauea, HI (US); Jeanne A. Ruiz, Sunnyvale, CA (US); Lorne E. Bechtel, Los Altos, CA (US)

(73) Assignee: Molecular Devices Corporation, Sunnyvale, CA (US)

( * ) Notice: Subject to any disclaimer, the term of this patent is extended or adjusted under 35 U.S.C. 154(b) by 214 days.

(21) Appl. No.: 09/710,061

(22) Filed: Nov. 10, 2000

Related U.S. Application Data

(60) Provisional application No. 60/164,633, filed on Nov. 10, 1999.

(51) Int. Cl.$^7$ ............................................. G01N 21/00
(52) U.S. Cl. ......................................... 356/73; 235/454
(58) Field of Search ........................... 250/227.22, 205, 250/227.23, 227.24, 227.11, 227.14, 227.21; 356/244, 246, 73; 385/12, 13, 115, 117, 118

(56) References Cited

U.S. PATENT DOCUMENTS

| | | |
|---|---|---|
| 2,719,214 A | 9/1955 | Potter |
| 3,013,467 A | 12/1961 | Minsky |
| 3,423,581 A | 1/1969 | Baer |
| 3,516,736 A | 6/1970 | Weaver |
| 3,849,654 A | 11/1974 | Malvin |
| 3,885,162 A | 5/1975 | Geertz |
| 3,932,023 A | 1/1976 | Humer |
| 4,011,451 A | 3/1977 | Nelson |
| 4,067,653 A | 1/1978 | Fletcher et al. |
| 4,074,939 A | 2/1978 | Rabl |
| 4,076,420 A | 2/1978 | De Maeyer et al. |
| 4,100,416 A | 7/1978 | Hirschfeld |
| 4,144,452 A | 3/1979 | Harte |
| 4,150,870 A | 4/1979 | d'Auria |
| 4,203,670 A | 5/1980 | Bromberg |

(List continued on next page.)

FOREIGN PATENT DOCUMENTS

| | | |
|---|---|---|
| EP | 0 266 881 A2 | 5/1988 |
| EP | 0 259 386 B1 | 6/1990 |

(List continued on next page.)

OTHER PUBLICATIONS

*Standard Handbook for Electrical Engineers*, Fink et al., pp. 22–2 through 25–5 (11$^{th}$ ed. 1978).
*Fundamentals of Light Microscopy*, Spencer, Cambridge University Press, 1982.

(List continued on next page.)

*Primary Examiner*—Karl D. Frech
(74) *Attorney, Agent, or Firm*—Kolisch Hartwell, P.C.

(57) ABSTRACT

Apparatus and methods for combining multiple modes and methods of optical detection, postprocessing, and/or feedback loops in bioanalytical measurements. The methods may include (1) positioning a composition at an examination site in a multi-mode instrument; (2) detecting light transmitted form the composition using the multi-mode instrument in a first optical measurement mode; (3) detecting light transmitted from the composition using the multi-mode instrument in a second optical measurement mode, the second mode being different than the first mode; and (4) computing a quantity related to a property of the composition using the light detected in at least one of the optical measurement modes. These steps may be performed on one or more samples, simultaneously and/or sequentially. The quantity may relate to photoluminescence, chemiluminescence, absorption, and/or scattering, among others.

28 Claims, 7 Drawing Sheets

U.S. PATENT DOCUMENTS

| | | |
|---|---|---|
| 4,240,751 A | 12/1980 | Linnecke et al. |
| 4,296,326 A | 10/1981 | Haslop et al. |
| 4,341,957 A | 7/1982 | Wieder |
| 4,397,560 A | 8/1983 | Andresen |
| 4,451,149 A | 5/1984 | Noeller |
| 4,451,433 A | 5/1984 | Yamashita et al. |
| 4,485,430 A | 11/1984 | Achiaga Fustel |
| 4,501,970 A | 2/1985 | Nelson |
| 4,567,847 A | 2/1986 | Linner |
| 4,591,550 A | 5/1986 | Hafeman et al. |
| 4,626,684 A | 12/1986 | Landa |
| 4,646,214 A | 2/1987 | Mendleski |
| 4,685,801 A | 8/1987 | Minekane |
| 4,699,512 A | 10/1987 | Koshi |
| 4,704,255 A | 11/1987 | Jolley |
| 4,704,353 A | 11/1987 | Humphries et al. |
| 4,707,067 A | 11/1987 | Haberland et al. |
| 4,724,217 A | 2/1988 | Miller |
| 4,730,921 A | 3/1988 | Klein et al. |
| 4,737,464 A | 4/1988 | McConnell et al. |
| 4,738,825 A | 4/1988 | Kelln et al. |
| 4,741,619 A | 5/1988 | Humphries et al. |
| 4,753,501 A | 6/1988 | Battle |
| 4,758,786 A | 7/1988 | Hafeman |
| 4,762,420 A | 8/1988 | Bowley |
| 4,772,453 A | 9/1988 | Lisenbee |
| 4,784,275 A | 11/1988 | Fridge |
| 4,801,804 A | 1/1989 | Rosenthal |
| 4,802,768 A | 2/1989 | Gifford et al. |
| 4,808,828 A | 2/1989 | Kitamori et al. |
| 4,810,096 A | 3/1989 | Russell et al. |
| 4,826,660 A | 5/1989 | Smith et al. |
| 4,849,330 A | 7/1989 | Humphries et al. |
| 4,855,930 A | 8/1989 | Chao et al. |
| 4,868,103 A | 9/1989 | Stavrianopoulos et al. |
| 4,873,633 A | 10/1989 | Mezei et al. |
| 4,877,965 A | 10/1989 | Dandliker et al. |
| 4,883,579 A | 11/1989 | Humphries et al. |
| 4,885,087 A | 12/1989 | Kopf |
| 4,892,409 A | 1/1990 | Smith |
| 4,897,548 A | 1/1990 | Döme et al. |
| 4,911,794 A | 3/1990 | Parce et al. |
| 4,915,812 A | 4/1990 | Parce et al. |
| 4,923,819 A | 5/1990 | Fernandez et al. |
| 4,931,402 A | 6/1990 | Abplanalp |
| 4,936,682 A | 6/1990 | Hoyt |
| 4,948,442 A | 8/1990 | Manns |
| 4,963,815 A | 10/1990 | Hafeman |
| 4,968,148 A | 11/1990 | Chow et al. |
| 4,979,821 A | 12/1990 | Schutt et al. |
| 5,009,488 A | 4/1991 | Fay et al. |
| 5,018,866 A | 5/1991 | Osten |
| 5,020,995 A | 6/1991 | Levy |
| 5,034,613 A | 7/1991 | Denk et al. |
| 5,039,219 A | 8/1991 | James et al. |
| 5,047,215 A | 9/1991 | Manns |
| 5,058,045 A | 10/1991 | Ma |
| 5,082,628 A | 1/1992 | Andreotti et al. |
| 5,084,246 A | 1/1992 | Lyman et al. |
| 5,091,652 A | 2/1992 | Mathies et al. |
| 5,095,517 A | 3/1992 | Monguzzi et al. |
| 5,096,807 A | 3/1992 | Leaback |
| 5,104,804 A | 4/1992 | Humphries et al. |
| 5,112,134 A | 5/1992 | Chow et al. |
| 5,160,702 A | 11/1992 | Kopf-Sill et al. |
| 5,164,319 A | 11/1992 | Hafeman et al. |
| 5,169,601 A | 12/1992 | Ohta et al. |
| 5,192,510 A | 3/1993 | Zoha et al. |
| 5,196,709 A | 3/1993 | Berndt et al. |
| 5,198,670 A | 3/1993 | VanCauter et al. |
| 5,206,568 A | 4/1993 | Björnson et al. |
| 5,208,161 A | 5/1993 | Saunders et al. |
| 5,208,651 A | 5/1993 | Buican |
| 5,216,488 A | 6/1993 | Tuunanen et al. |
| 5,225,164 A | 7/1993 | Astle |
| 5,257,202 A | 10/1993 | Feddersen et al. |
| 5,270,788 A | 12/1993 | Cercek et al. |
| 5,273,718 A | 12/1993 | Sköld et al. |
| 5,275,951 A | 1/1994 | Chow et al. |
| 5,278,048 A | 1/1994 | Parce et al. |
| 5,281,825 A | 1/1994 | Berndt et al. |
| 5,289,407 A | 2/1994 | Strickler et al. |
| 5,307,144 A | 4/1994 | Hiroshi et al. |
| 5,315,015 A | 5/1994 | Hui et al. |
| 5,317,485 A | 5/1994 | Merjanian |
| 5,319,436 A | 6/1994 | Manns et al. |
| 5,323,008 A | 6/1994 | Studholme et al. |
| 5,323,010 A | 6/1994 | Gratton et al. |
| 5,340,716 A | 8/1994 | Ullman et al. |
| 5,340,747 A | 8/1994 | Eden |
| 5,341,215 A | 8/1994 | Seher |
| 5,353,112 A | 10/1994 | Smith |
| 5,355,215 A | 10/1994 | Schroeder et al. |
| 5,357,095 A | 10/1994 | Weyrauch et al. |
| 5,361,626 A | 11/1994 | Colligan et al. |
| 5,384,093 A | 1/1995 | Ootani et al. |
| 5,395,503 A | 3/1995 | Parce et al. |
| 5,401,465 A | 3/1995 | Smethers et al. |
| 5,418,371 A | 5/1995 | Aslund et al. |
| 5,420,408 A | 5/1995 | Weyrauch et al. |
| 5,436,718 A | 7/1995 | Fernandes et al. |
| 5,448,935 A | 9/1995 | Kosinar |
| 5,449,921 A | 9/1995 | Baba |
| 5,457,527 A | 10/1995 | Manns et al. |
| 5,459,300 A | 10/1995 | Kasman |
| 5,480,804 A | 1/1996 | Niwa et al. |
| 5,485,530 A | 1/1996 | Lakowicz et al. |
| 5,487,872 A | 1/1996 | Hafeman et al. |
| 5,491,343 A | 2/1996 | Brooker |
| 5,496,697 A | 3/1996 | Parce et al. |
| 5,500,188 A | 3/1996 | Hafeman et al. |
| 5,504,337 A | 4/1996 | Lakowicz et al. |
| 5,512,492 A | 4/1996 | Herron et al. |
| 5,523,573 A | 6/1996 | Hänninen et al. |
| 5,527,684 A | 6/1996 | Mabile et al. |
| 5,528,046 A | 6/1996 | Ishikawa |
| 5,529,752 A | 6/1996 | Pontis et al. |
| 5,537,343 A | 7/1996 | Kikinis et al. |
| 5,541,113 A | 7/1996 | Siddigi et al. |
| 5,542,012 A | 7/1996 | Fernandes et al. |
| 5,557,398 A | 9/1996 | Wechsler et al. |
| 5,561,068 A | 10/1996 | Rounbehler et al. |
| 5,567,302 A | 10/1996 | Song et al. |
| 5,589,136 A | 12/1996 | Northrup et al. |
| 5,589,350 A | 12/1996 | Bochner |
| 5,589,351 A | 12/1996 | Harootunian |
| 5,592,289 A | 1/1997 | Norris |
| 5,593,867 A | 1/1997 | Walker et al. |
| 5,595,710 A | 1/1997 | Van Dusen et al. |
| 5,599,500 A | 2/1997 | Jones |
| 5,604,130 A | 2/1997 | Warner et al. |
| 5,620,894 A | 4/1997 | Barger et al. |
| 5,626,134 A | 5/1997 | Zuckerman |
| 5,631,734 A | 5/1997 | Stern et al. |
| 5,633,724 A | 5/1997 | King et al. |
| 5,635,402 A | 6/1997 | Alfano et al. |
| 5,641,633 A | 6/1997 | Linn et al. |
| 5,645,800 A | 7/1997 | Masterson et al. |
| 5,663,545 A | 9/1997 | Marquiss |
| 5,670,113 A | 9/1997 | Akong et al. |
| 5,672,880 A | 9/1997 | Kain |

| | | | |
|---|---|---|---|
| 5,676,943 A | 10/1997 | Baetge et al. | |
| 5,677,196 A | 10/1997 | Herron et al. | |
| 5,679,310 A | 10/1997 | Manns | |
| 5,736,410 A | 4/1998 | Zarling et al. | |
| 5,738,825 A | 4/1998 | Rudigier et al. | |
| 5,741,554 A | 4/1998 | Tisone | |
| 5,746,974 A | 5/1998 | Massey et al. | |
| 5,750,410 A | 5/1998 | Dou et al. | |
| 5,756,292 A | 5/1998 | Royer | |
| 5,760,900 A * | 6/1998 | Ito et al. ..................... | 356/338 |
| 5,766,875 A | 6/1998 | Hafeman et al. | |
| 5,780,857 A | 7/1998 | Harju et al. | |
| 5,798,083 A | 8/1998 | Massey et al. | |
| 5,798,085 A | 8/1998 | Seaton et al. | |
| 5,825,617 A | 10/1998 | Kochis et al. | |
| 5,842,582 A | 12/1998 | DeStefano, Jr. | |
| 5,888,454 A | 3/1999 | Leistner et al. | |
| 5,905,571 A | 5/1999 | Butler et al. | |
| 5,933,232 A | 8/1999 | Atzler et al. | |
| 5,959,738 A | 9/1999 | Hafeman et al. | |
| 5,989,835 A | 11/1999 | Dunlay et al. | |
| 5,993,746 A | 11/1999 | Priha et al. | |
| 6,020,591 A | 2/2000 | Harter et al. | |
| 6,025,985 A | 2/2000 | Leytes et al. | |
| 6,033,100 A | 3/2000 | Marquiss et al. | |
| 6,071,748 A | 6/2000 | Modlin et al. | |
| 6,097,025 A * | 8/2000 | Modlin et al. .............. | 250/205 |
| 6,137,584 A | 10/2000 | Seidel et al. | |
| 6,159,425 A | 12/2000 | Edwards et al. | |
| 6,187,267 B1 | 2/2001 | Taylor et al. | |

FOREIGN PATENT DOCUMENTS

| | | |
|---|---|---|
| EP | 0 977 037 A1 | 2/2000 |
| EP | 0 993 916 A2 | 4/2000 |
| EP | 0 995 555 A1 | 4/2000 |
| EP | 1 003 020 A1 | 5/2000 |
| EP | 1 003 039 A1 | 5/2000 |
| GB | 2 215 838 A | 9/1989 |
| GB | 2 228 081 A | 8/1990 |
| WO | WO 99/04228 | 1/1999 |
| WO | WO 99/08233 | 2/1999 |
| WO | WO 99/23466 | 5/1999 |
| WO | WO 99/37203 | 7/1999 |
| WO | WO 99/42817 | 8/1999 |
| WO | WO 99/54711 | 10/1999 |
| WO | WO 00/04364 | 1/2000 |
| WO | WO 00/06989 | 2/2000 |
| WO | WO 00/06990 | 2/2000 |
| WO | WO 00/06991 | 2/2000 |
| WO | WO 00/42209 | 7/2000 |
| WO | WO 00/50877 | 8/2000 |
| WO | WO 00/55372 | 9/2000 |
| WO | WO 00/66269 | 11/2000 |
| WO | WO 01/04608 | 1/2001 |

OTHER PUBLICATIONS

*Prinicples of Fluorescence Spectroscopy*, Lakowicz, First Edition, Sep. 1983.
*Basic Fluorescence Microscopy*, Taylor et al., *Methods in Cell Biology*, vol. 29, pp. 207–237, 1989.
*Quantitative Fluorescence Microscopy Using Photomultiplier Tubes and Imaging Detectors*, Wampler et al., *Methods in Cell Biology*, vol. 29, pp. 239–267, 1989.
*Three–Dimensional Confocal Fluorescence Microscopy*, Brakenhoff et al., *Methods in Cell Biology*, vol. 30, pp. 379–389, 1989.
*Laser Scanning Confocal Microscopy of Living Cells*, Lemasters et al., *Optical Microscopy: Emerging Methods and Applications*, pp. 339–345, 1993.

*Time–Resolved Fluorescence Lifetime Imaging*, vandeVen et al., *Optical Microscopy: Emerging Methods and Applications*, pp. 373–389, 1993.
*Electrochemiluminescence: A New Diagnostic and Research Tool*, Yang et al., *Bio/Technology*, vol. 12, pp. 193–194, Feb. 1994.
*Sorting Single–Molecules: Application to Diagnostics and Evolutionary Biotechnology*, Eigen et al., *PNAS*, vol. 91, pp. 5740–5747, 1994.
*High Throughput Screening Using Dynamic Fluorescence*, Swift et al., *SPIE*, vol. 2388, pp. 182–189, Feb. 6–8, 1995.
*A Lifetime–Based Optical Co, Gas Sensor With Blue or Red Excitation and Stokes or Anti–Stokes Detection*, Sipior et al., *Analytical Biochemistry*, vol. 227, pp. 309–318 (1995).
Genesis Series Rebotic Sample Processors brochure, Tecan AG, Oct. 1997.
A Measure of Brilliance, TR717 Microplate Luminometer brochure, Tropix, Inc., 1997.
Advanced Microplate Detection Systems brochure, Tecan AG, Feb. 1998.
The Spectra Family brochure, Tecan AG, Feb. 1998.
Assist Plate Handling Device brochure, Labsystems, May 1998.
Tecan Spectrafluor—A Step Forward in Microplate Fluorometry, internet description pages, printed from internet on Jun. 17, 1998.
Wallac Time–Resolved Fluorometry—The Key to Improved Assay Sensitivity, internet description pp., Jul. 7, 1998.
Wallac 1234 DELFIA Fluorometer, internet description page, Jul. 7, 1998.
Wallac 1420 Victor Multilabel Counter, internet description pages, Jul. 7, 1998.
Wallac 1420 Vitor$^2$ Multilabel Counter, interent description pages, Jul. 7, 1998.
Wallac 1442 Arthur Multi–Wavelength Fluoroimager, internet description page, Jul. 7, 1998.
Wallac Labelling Reagents for Time–Resolved Fluorometry, internet description page, Jul. 7, 1998.
Genesis Assay Workstation brochure, Tecan AG, Jul. 1998.
Genesis Logistics Workstation brochure, Tecan AG, Jul. 1998.
Polarion brochure, Tecan AG, Aug. 1998.
CytoFluor Fluorescence Multi–Well Plate Reader brochure, PerSeptive Biosystems, 1998.
Microplate Instrumentation Catalogue 1998, Labsystems, 1998.
*Fixed Polarizer Ellipsometry for Simple and Sensitive Detection of Thin Films Generated by Specific Molecular Interactions: Applications in Immunoassays and DNA Sequence Detection*, Ostroff et al., *Clinical Chemistry*, vol. 44, No. 9, pp. 2031–2035, 1998.
Magellan, Instrument Control and Data Analysis Software brochure, Tecan AG, Nov. 1999.
Twister™, Tecan's Automated Microplate Handler brochure, Tecan AG, Nov. 1999.
*A Microfabricated Fluorescence–activated Cell Sorter*, Fu et al., *Nature Biotechnology*, vol. 17, pp. 1109–1111, Nov. 1999.
Absorbance Reader brochure, Tecan AG, Dec. 1999.
Ultra—The Solution for HTS and Assay Development brochure, Tecan Austria GmbH, Dec. 1999.
*Principles of Fluorescence Spectroscopy*, Lakowicz, Second Edition, 1999.
CyBi™—Lumax 1536 brochure, CyBio AG, May 2000.

CyBi™—PlateSafe brochure, CyBio AG, May 2000.

SPECTRAmax® Gemini XS brochure, Molecular Devices Corp., Jun. 2000.

Packard BioScience Company Introduces the Fusion™ Universal Microplate Analyzer press release, Packard BioScience Company, Jun. 29, 2000.

SPECTRAmax® Plus[384] brochure, Molecular Devices Corp., Jun. 2000.

Labcyte: Research and Clinical Instruments for Life Scineces brochure, Arlena Research LLC, Aug. 1, 2000.

Fusion™, Universal Microplate Analyzer, Packard BioScience Company, Aug. 2000.

CyBi™–Screen–Machine: One System—Many Solutions brochure, CyBio AG, 2000.

Acumen Explorer brochure, Acumen, undated.

FLIPR 384: Essential Technology for Drug Discovery brochure, Molecular Devices Corp., undated.

FLUOstar Galaxy brochure, BMG Labtechnologies GmbH, undated.

NEPHELOstar brochure, BMG Labtechnologies GmbH, undated.

LUMIstar Galaxy brochure, BMG Labtechnologies GmbH, undated.

POLARstar Galaxy brochure, BMG Labtechnologies GmbH, undated.

POLARstar Galaxy flyer, BMg Labtechnologies GmbH, undated.

* cited by examiner ously filed U.S. patent application Ser. No. 09/302,158 — omitted; reproducing visible content:

MULTI-MODE LIGHT DETECTION SYSTEM

CROSS-REFERENCES TO PRIORITY APPLICATIONS

This application is based upon and claims priority from U.S. Provisional Patent Application Ser. No. 60/164,633, filed Nov. 10, 1999, now abandoned.

This application also is a continuation-in-part of the following U.S. patent applications: Ser. No. 09/302,158, file Apr. 29, 1999 now U.S. Pat. No 6,576,476 and Ser. No. 09/629,599, filed Jul. 31, 2000, now U.S. Pat. No. 6,469,311.

U.S. patent application Ser. No. 09/302,158, in turn, is divisional continuation application of U.S. patent application Ser. No. 09/146,081, filed Sep. 2, 1998, now U.S. Pat. No. 6,187,267. The '081 application, in turn, is a continuation of the following patent applications: U.S. patent application Ser. No. 09/062,472, filed Apr. 17, 1998, now U.S. Pat. No. 6,071,748; PCT Patent Application Serial No. PCT/US98/14575, filed Jul. 15, 1998, now abandoned; U.S. patent application Ser. No. 09/118,141, filed on Jul. 16, 1998, now U.S. Pat. No. 6,313,960; U.S. patent application Ser. No. 09/118,310, filed Jul. 16, 1998, now U.S. Pat. No. 6,033,100; U.S. patent application Ser. No. 09/118,341, filed Jul. 16, 1998, now U.S. Pat. No. 6,025,985; U.S. patent application Ser. No. 09/144,575, filed Aug. 31, 1998, now U.S. Pat. No. 6,159,425; and U.S. patent application Ser. No. 09/144,578, filed Aug. 31, 1998 U.S. Pat. No. 6,499,366. These parent applications, in turn, claim priority from additional applications, as identified therein. The '081 application, in turn, also (directly and/or through its parent applications) is based upon and claims benefit under 35 U.S.C. § 119(e) of the following U.S. provisional patent applications, each of which is now abandoned: Ser. No. 60/052,876, filed Jul. 16, 1997; Ser. No. 60/059,639, filed Sep. 20, 1997; Ser. No. 60/063,811, filed Oct. 31, 1997; Ser. No. 60/072,499, filed Jan. 26, 1998; Ser. No. 60/072,780, filed Jan. 27, 1998; Ser. No. 60/075,414, filed Feb. 20, 1998; Ser. No. 60/075,806, filed Feb. Ser. No. 60/082,253, filed Apr. 17, 1998; Ser. No. 60/084,167, filed May 4, 1998; Ser. No. 60/085,335, filed May 13, 1998; Ser. No. 60/085,500, filed May 14, 1998; Ser. No. 60/089,848, filed Jun. 19, 1998; Ser. No. 60/094,275, filed Jul. 27, 1998; Ser. No. 60/094,276, filed Jul. 27, 1998; and Ser. No. 60/094,306, filed Jul. 27, 1998.

U.S. patent application Ser. No. 09/629,599, in turn, is a continuation of U.S. patent application Ser. No. 09/160,533, filed Sep. 24, 1998, now U.S. Pat. No. 6,097,025. The '533 application. in turn, is a continuation of the following patent applications: U.S. patent application Ser. No. 09/062,472, filed Apr. 17, 1998, now U.S. Pat. No. 6,071,748; PCT Patent Application Serial No. PCT/US98/14575, filed Jul. 15, 1998, now abandoned; U.S. patent application Ser. No. 09/118,141, filed Jul. 16, 1998, now U.S. Pat. No. 6,313,960; U.S. patent application Ser. No. 09/118,310, filed Jul. 16, 1998, now U.S. Pat. No. 6,033,100; U.S. patent application Ser. No. 09/118,341, filed Jul. 16, 1998, now U.S. Pat. No. 6,025,985; U.S. patent application Ser. No. 09/144,575, filed Aug. 31, 1998, now U.S. Pat. No. 6,159,425; U.S. patent application Ser. No. 09/144,578, filed Aug. 31, 1998; U.S. patent application Ser. No. 09/146,081, filed Sep. 2, 1998, now U.S. Pat. No. 6,187,267; U.S. patent application Ser. No. 09/156,318, filed Sep. 18, 1998, now U.S. Pat. No. 6,258,326; and U.S. patent application Ser. No. 09/478,819, filed Jan. 5, 2000, now U.S. Pat. No. 6,488,892. These parent applications, in turn, claim priority from additional applications, as identified therein. The '533 application, in turn, also (directly and/or through its parent applications) is based upon and claims benefit under 35 U.S.C. § 119(e) of the following U.S. provisional patent applications, each of which is now abandoned: Ser. No. 60/063,811, filed Oct. 31, 1997; Ser. No. 60/072,499, filed Jan. 26, 1998; Ser. No. 60/072,780, filed Jan. 27, 1998; Ser. No. 60/075,414, filed Feb. 20, 1998; Ser. No. 60/075,806, filed Feb. Ser. No. 60/082,253, filed Apr. 17, 1998; Ser. No. 60/084,167, filed May 4, 1998; Ser. No. 60/085,335, filed May 13, 1998; Ser. No. 60/085,500, filed May 14, 1998; Ser. No. 60/089,848, filed Jun. 19, 1998; Ser. No. 60/094,275, filed Jul. 27, 1998; Ser. No. 60/094,276, filed Jul. 27, 1998; Ser. No. 60/094,306, filed Jul. 27, 1998; Ser. No. 60/100,817, filed Sep. 18, 1998; and Ser. No. 60/100,951, filed Sep. 18, 1998.

Cross-References to Additional Materials

This application incorporates by reference in their entirety for all purposes the following patents and patent applications: U.S. Pat. No. 6,097,025, issued Aug. 1, 2000, U.S. Pat. No. 5,355,215, issued Oct. 11, 1994; U.S. patent application Ser. No. 08/840,553, filed Apr. 14, 1997; U.S. patent application Ser. No. 09/156,318, filed Sep. 18, 1998; U.S. patent application Ser. No. 09/349,733, filed Jul. 8, 1999; U.S. patent application Ser. No. 09/337,623, filed Aug. 16, 1999; U.S. patent application Ser. No. 09/478,819, filed Jan. 5, 2000; and U.S. patent application Ser. No. 09/643,221, filed Aug. 18, 2000.

This application also incorporates by reference the following PCT Patent Applications: Serial No. PCT/US99/16453, filed Jul. 21, 1999, published as WO 00/05336 on Feb. 3, 2000 (included herewith as Appendix A); Serial No. PCT/US00/12277, published as WO 00/66269, on Nov. 9, 2000 (included herewith as Appendix B), filed May 3, 2000; and Serial No. PCT/US00/18547, filed Jul. 7, 2000, published as WO 01/04608 on Jan. 18, 2001 (included herewith as Appendix C).

This application also incorporates by reference the following publications: Joseph R. Lakowicz, *Principles of Fluorescence Spectroscopy* ($2^{nd}$ ed. 1999); and Bob Sinclair, *Everything's Great When It Sits on a Chip: A Bright Future for DNA Arrays,* 13 THE SCIENTIST, May 24, 1999, at 18.

TECHNICAL FIELD

The invention relates to apparatus and methods for optical detection. More particularly, the invention relates to apparatus and methods for combining multiple modes and methods of optical detection, postprocessing, and/or feedback loops in bioanalytical measurements.

BACKGROUND OF THE INVENTION

The number of bioanalytical measurements performed in life science research is increasing dramatically. This increase is driven in part by advances in genomics and combinatorial chemistry, which have increased both the number of biological targets and the number of compounds for screening them. This increase also is driven in part by advances in assay technologies, especially relating to DNA interactions, protein and peptide interactions, and cell-based assays, which have pushed the number of bioanalytical measurements from hundreds in standard 96-well microplates to millions in even higher-density microplates.

The cost of bioanalytical measurements is roughly proportional to the amount of regent consumed and to the time spent preparing the reagents, performing the measurements, and analyzing the data. To reduce cost in these measurements, researchers are adopting homogeneous assays and miniaturizing assay volumes. Homogeneous (i.e., "mix and measure") assays generally do not involve filtration steps, which add to the complexity and cost of the measurements. Miniaturizing assay volumes (i.e., miniaturization) generally involves a decrease in assay volume (typically from about 100–200 $\mu$L to about 1–10 $\mu$L) and/or an increase in microplate well density (typically from 96-well formats to 384, 864, 1536, 3456, or denser formats).

Although miniaturization can be an effective cost reduction strategy, smaller sample sizes and larger numbers of measurements generally require larger numbers of secondary measurements to validate the results of the primary measurements. Ideally, the primary measurements should not require secondary analysis; however, false positives must be identified and eliminated. In addition, it is desirable to reduce the frequency of false negatives because these constitute lost information. For example, in the high-throughput screening typically carried out in drug discovery operations, false positives must be identified and eliminated in secondary operations because, by definition, they will not lead to a viable drug. Additionally, false negatives result in an inability to collect information from the affected library compounds.

SUMMARY OF THE INVENTION

The invention provides apparatus and methods for combining multiple modes and methods of optical detection, postprocessing, and/or feedback loops in bioanalytical measurements.

BRIEF DESCRIPTION OF ACCOMPANYING MATERIALS

DETAILED DESCRIPTION OF THE INVENTION

Figure 1:
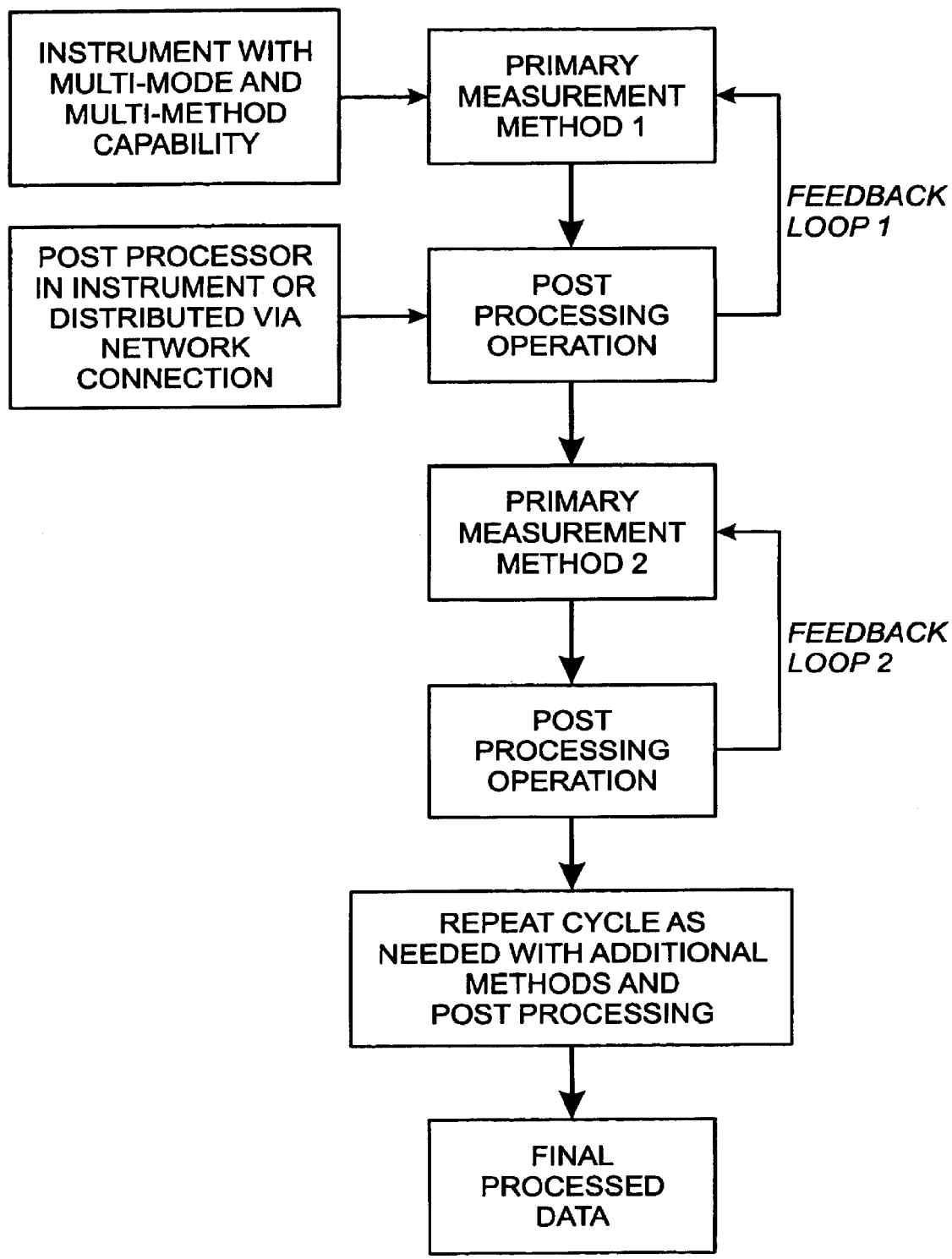
FIG. 1 is a flowchart showing how aspects of the invention may be used and/or combined to combine modes, methods, postprocessing, and feedback loops in optical detection.

The invention provides apparatus and methods for performing and/or combining multiple modes and methods of optical detection, postprocessing, and/or feedback loops in bioanalytical measurements. These apparatus and methods may involve multi-mode instruments and a plurality of optical measurement modes. The apparatus and methods may be used to identify and/or correct for measurement errors, reducing the frequency of false positives and false negatives. The apparatus and methods also may be used to enable new assays.

Suitable multi-mode instruments and optical measurement modes are described in subsequent sections and in the patents and patent applications incorporated herein by reference, particularly U.S. Provisional Patent Application Ser. No. 60/164,633, filed Nov. 10, 2000. Suitable instruments include point-reading (e.g., PMT-based) and image-reading (e.g., CCD-based) optical devices. Suitable modes include generally include any mode or method for performing an optical measurement, including photoluminescence, chemiluminescence, absorption, and scattering, among others. These modes include time-resolved and steady-state photoluminescence, including lifetime, intensity, polarization, energy transfer, and total internal reflection. These modes also include trans-absorption, epi-absorption, and trans-flectance. These modes also may include collecting an excitation and/or emission spectrum, for example, by scanning the excitation and/or emission wavelength while holding the other wavelength fixed. Suitable methods include all possible variations in optics and instrument settings to execute these modes and to improve signal detection, including FLARe™ methods of utilizing lamp modulation frequency and phase-and-modulation data to recover signal and suppress background.

The invention may involve use of two or more different optical measurement modes. Here, modes may be regarded as different if (1) each involves detecting a different property of light (e.g., intensity, polarization, etc.), and/or (2) each involves detecting light created by a different mechanism (e.g., photoluminescence, chemiluminescence, etc.), and/or (3) each involves detecting light modified by a different mechanism (e.g., absorption, scattering, etc.). Multiple measurements performed using a single method are not regarded as multiple modes, for example, measurements made at two different polarizer settings in a polarization assay, or measurements made at two different wavelengths in an energy-transfer or ratio-imaging assay, or measurements made using the same settings to obtain error statistics.

The invention permits the use of multiple detection modes and methods during one or more measurement cycles. For example, a set of methods can be performed on a microplate on a per-well, per-row, per-column, or per-plate basis. Postprocessing can be performed after the results of the first method are collected. One or more additional methods can be subsequently performed based on the results of each successive measurement. Additionally, each measurement or group of measurements can be analyzed in real time, and actions can be initiated based on the analysis of the data. For example, the mean and standard deviation of the fluorescence intensity can be determined for a population of samples or alternatively supplied as input by the user. A postprocessing operation can compare the data obtained from the samples to an acceptable window (or, equivalently, to an unacceptable window), for example, by using a database or look-up table. If the value is too high, a fluorescent contaminant may be present. If the value is too low, a pipetting error may have occurred such that a bubble is present in the well or a reagent is missing. Once it is determined that data values are out of range, a decision can be made automatically to alert a human operator (e.g., to conduct a visual examination) or to perform a pre-programmed task (e.g., such as halting operation of the instrument or system in which it is contained).

FIG. 1 is a flowchart showing more generally how different aspects of the invention may be used and/or combined to combine modes, methods, postprocessing, and feedback loops, and to enable some special functions. For example, information from a first method (Method 1) could be postprocessed, and a decision could be made to halt Method 1 or to re-measure or correct new data points using Method 1 or another method. Information from a second method (Method 2) could be used to detect a problem in Method 1, or vice-versa. For example, Method 2 could be a measurement of the fluorescence intensity of a critical reagent that has been colored with a fluorescent tag, such that a signal that is too high or too low in Method 2 could indicate a pipetting failure that adversely affects Method 1. Another application might be to have two or more targets in each well, such that each target is probed by a different assay and a different method. Another application might be to use a first method to obtain predicate information for a second method, such as using absorption at a first (e.g., infrared) wavelength to determine wavelength to determine path length before doing a measurement to determine an extinction coefficient.

Generally, optical measurements can be combined in various ways to detect (and sometimes also to correct) errors or interferences in assays, including those designed to screen samples (library compounds or natural products) in drug discovery. Some sources of interference are inherent to the sample, including optical absorption (also called "color quenching"), fluorescence, light scattering, static or dynamic quenching of fluorescent label, and enhancement of the label's fluorescence. Other interferences result from the properties of the assay in a particular sample holder, examples include air bubbles, meniscus irregularities, pipetting failure, and imperfections in the holder.

Combining non-luminescence and other methods can be useful. For example, combining an absorption measurement with a luminescence-intensity measurement permits the detection of color quenching and/or the presence of a contaminant. Likewise, combining a light-scattering measurement with a measurement made in another mode permits the detection of interferences due to turbidity in the assay well. In these cases, it is possible to go beyond detection to correction of the interference, by using the secondary measurement to construct a theoretically or empirically based correction factor for the primary measurement.

Combining fluorescence-polarization and fluorescence-intensity measurements can also be useful. Background fluorescence, especially sample fluorescence, interferes with fluorescence polarization measurements: the polarization is an intensity-weighted average of signal and background polarizations, which generally have different values. The overall fluorescence intensity of a sample is proportional to the sum of the intensity detected with parallel polarizers and twice the intensity detected with perpendicular polarizers. Hence, it is possible to synthesize the overall fluorescence intensity from the components of a fluorescence-polarization measurement. If this intensity is higher than control values in wells without sample, the sample must be contributing background fluorescence, and the fluorescence-polarization measurement is suspect.

For fluorescence-intensity assays, interfering background fluorescence is unlikely to have the same spectral and lifetime characteristics as the label. In the presence of such background, an additional measurement at a different excitation or emission wavelength somewhat different from that of the main measurement would reveal behavior different from that obtained with only the label present. Likewise, the wavelengths could be kept constant, but the lifetime could be probed differently (different integration time-window in the time domain, or different modulation frequency in the frequency domain).

A fluorescence-intensity measurement can be supplemented with a lifetime measurement to detect dynamic quenching, which is attended by a decrease in lifetime.

These examples illustrate, without limitation, the general principle that adding a secondary measurement to an assay method can be used to detect the presence of interferences, independently of whether the method combines the results of the two measurements to yield an assay that has improved rejection of interference. Further aspects of the invention are described without limitation in the following sections: (1) optical measurement modes, (2) multi-mode instruments, and (3) selected examples.

A. Optical Measurement Modes

Optical assays typically involve the study of matter using electromagnetic radiation. These assays can be divided into three broad modes or categories—absorbance, scattering/reflectance, and luminescence—each of which can be further divided into additional modes. Absorbance assays involve relating the amount of incident light that is absorbed by a sample to the type and number of molecules in the sample. Absorbance assays are a powerful method for determining the presence and concentration of an analyte in a sample. Most commonly, absorbance is measured indirectly by studying the portion of incident light that is transmitted by the sample. Scattering assays are similar to absorbance assays, in that the measurement is based on the amount of incident light that emerges or is transmitted from the sample. However, in the case of scattering, the signal increases with the number of interactions, whereas, in the case of absorbance, the signal decreases (inversely) with the number of interactions. Luminescence assays involve electromagnetic emissions from a sample other than the incident light. In each mode, the measurements may be broad spectrum or wavelength-specific, depending on the particular mode.

1. Absorption Assays

Figure 2:
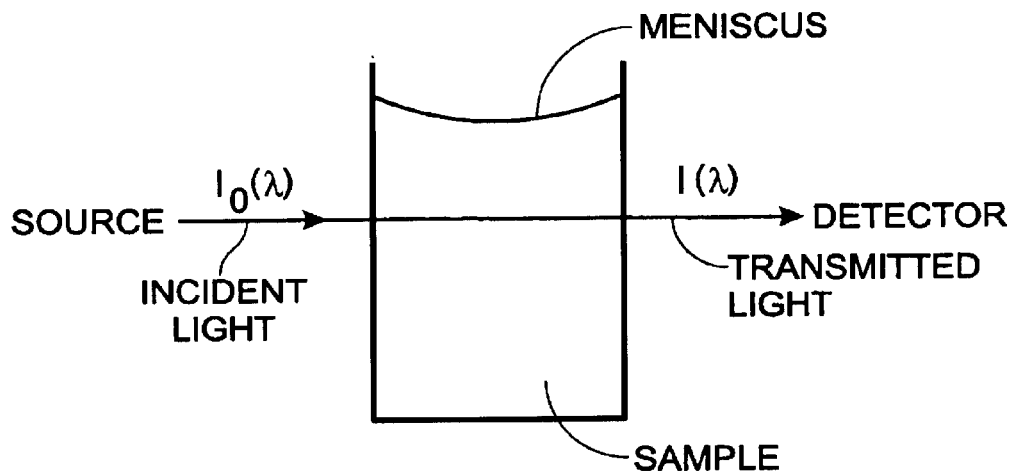
FIG. 2 is a schematic view of a typical absorbance experiment.

Absorption generally comprises the absorption of electromagnetic radiation by one or more components of a composition. FIG. 2 shows a schematic view of a typical absorption experiment, in which incident light is directed from a light source through a composition (and an associated holder), and transmitted light is measured using a detector. Absorption also can be measured using other optical arrangements, such as "epi-absorption," as described in PCT Patent Application Serial No. PCI/US99/16621, filed Jul. 23, 1999, published as WO 00/06991 on Feb. 10, 2000 (included herewith as Appendix D), which is incorporated herein by reference. The amount of light absorbed in passing through a position can be used to determine the identity, concentration, and electronic energy levels of components of the composition, among other properties.

The amount of light absorbed by a sample in an absorption experiment generally is described by the Beer-Lambert law:

$$\text{Absorbance} = -\log\left(\frac{I(\lambda)}{I_0(\lambda)}\right) = \varepsilon(\lambda)cl \qquad (1)$$

The Beer-Lambert law states that when light of wavelength $\lambda_e$ passes through an absorbing sample, its intensity, I, decreases exponentially. Here, $I_0(\lambda)$ is the intensity of the incident light at wavelength $\lambda$, $I(\lambda)$ is the intensity of the transmitted light, $\alpha(\lambda)$ is the decadic molar extinction coefficient, c is the concentration of absorbing molecules, and 1 is the path length. The quantity $-\log(I/I_0)$ is termed the absorbance and is the logarithm of the reciprocal of the fraction of transmitted light. Equation 1 shows that absorbance can be increased by increasing the path length and/or the concentration of absorbing molecules. Generally, absorbance measurements are most accurate when the absorbance is in the range 0.1–2.0, corresponding to absorption of about 20–99% of the incident light.

2. Scattering Assays

Scattering generally comprises the dispersal of electromagnetic radiation into a range of directions due to physical interactions of the radiation with a composition. Scattering assays can be used to detect the motion, size, concentration, and aggregation state of molecules or other scatterers in a sample, among other properties. For example, by observing the spectral spread of scattered light, the average velocity of scatterers can be determined. By observing the intensity of scattered light, the concentration of scatterers can be measured. By observing the angular distribution of scattered light, various physical characteristics of scatterers can be deduced. Here, the term "scattering sources" describes any molecule, particle, or other object capable of scattering radiation, individually and/or in aggregate.

3. Luminescence Assays

Luminescence is the emission of light from excited electronic states of atoms or molecules. Luminescence generally refers to all kinds of light emission, except incandescence, and may include photoluminescence, chemiluminescence, and electrochemiluminescence, among others. In photoluminescence, including fluorescence and phosphorescence, the excited electronic state is created by the absorption of electromagnetic radiation. In chemiluminescence, which includes bioluminescence, the excited electronic state is created by a transfer of chemical energy. In electrochemiluminescence, the excited electronic state is created by an electrochemical process.

Luminescence assays are assays that use luminescence emissions from luminescent analytes to study the properties and environment of the analyte, as well as binding reactions and enzymatic activities involving the analyte, among others. In this sense, the analyte may act as a reporter to provide information about another material or target substance that may be the focus of the assay. Luminescence assays may use various aspects of the luminescence, including its intensity, polarization, and lifetime, among others. Luminescence assays also may use time-independent (steady-state) and/or time-dependent (time-resolved) properties of the luminescence. Steady-state assays generally are less complicated than time-resolved assays, but generally yield less information.

Luminescence assays may be conducted using a variety of measurement modes, including chemiluminescence, fluorescence intensity (FLINT), fluorescence polarization (FP), fluorescence resonance energy transfer (FRET), fluorescence lifetime (FLT), total internal reflection fluorescence (TIRF), fluorescence correlation spectroscopy (FCS), and fluorescence recovery after photobleaching (FRAP), as well as their phosphorescence and higher-transition analogs, among others.

The remainder of this section describes without limitation four exemplary luminescence measurement modes: (a) intensity modes, (b) polarization modes, (c) energy transfer modes, and (d) steady-state and time-resolved modes.

a. Intensity Modes

Luminescence intensity assays involve monitoring the intensity (or amount) of light emitted from a composition. The intensity of emitted light will depend on the extinction coefficient, quantum yield, and number of the luminophores in the composition, among others. These quantities, in turn, will depend on the environment of the luminophore, among others, including the proximity and efficacy of quenchers and energy transfer partners. Thus, luminescence intensity assays may be used to study binding reactions, among other applications.

b. Polarization Modes

Luminescence polarization assays involve monitoring the intensity of polarized light emitted from a composition. (Polarization describes the direction of light's electric field, which generally is perpendicular to the direction of light's propagation.) Polarization assays typically are used to study molecular rotation and phenomena such as binding that affect rotation. Polarization assays may be homogeneous and ratiometric, making them relatively insensitive to sample-to-sample variations in concentration, volume, and meniscus shape.

Figure 3:
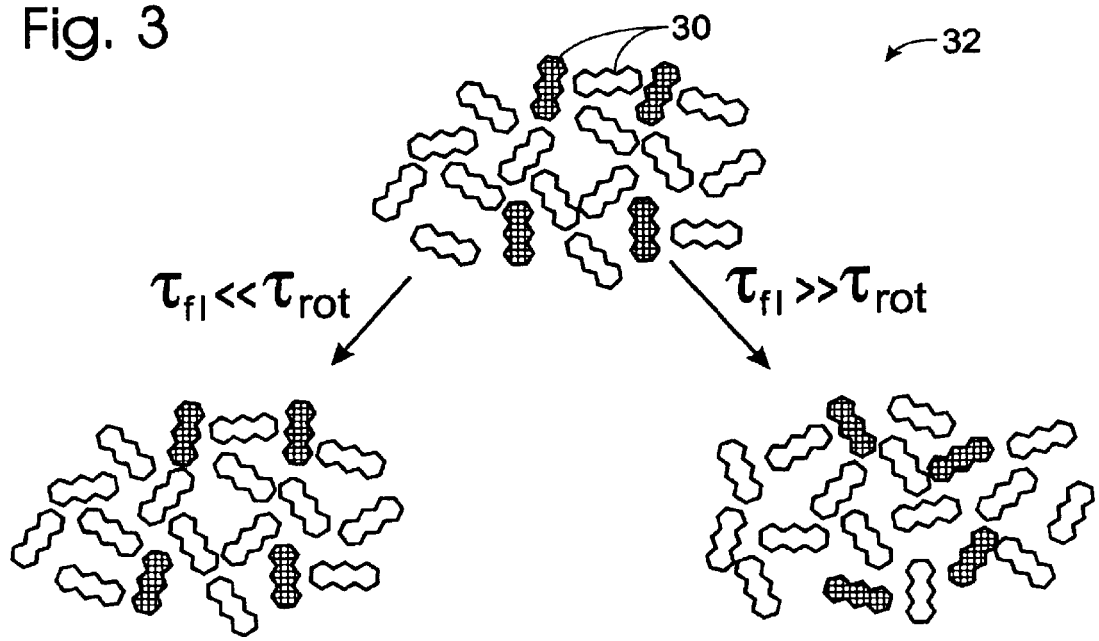
FIG. 3 is a schematic view of luminescently labeled molecules, showing how molecular reorientation affects luminescence polarization.

FIG. 3 is a schematic view showing how luminescence polarization is affected by molecular rotation. In a luminescence polarization assay, specific molecules 65 within a composition 66 are labeled with one or more luminophores. The composition then is illuminated with polarized excitation light, which preferentially excites luminophores having absorption dipoles aligned parallel to the polarization of the excitation light. These molecules subsequently decay by preferentially emitting light polarized parallel to their emission dipoles. The extent of polarization of the total emitted light depends on the extent of molecular reorientation during the time interval between luminescence excitation and emission, which is termed the luminescence lifetime, $\tau$. In turn, the extent of molecular reorientation depends on the luminescence lifetime and the size; shape, and environment of the reorienting molecule. Thus, luminescence polarization assays can be used to quantify binding/hybridization reactions and enzymatic activity, among other applications. In particular, molecules commonly rotate via diffusion with a rotational correlation time $\tau_{rot}$ that is proportional to their size. Thus, during their luminescence lifetime, relatively large molecules will not reorient significantly, so that their total luminescence will be relatively polarized. In contrast, during the same time interval, relatively small molecules will reorient significantly, so that their total luminescence will be relatively unpolarized.

The relationship between polarization and intensity is expressed by the following equation:

$$P = \frac{I_\| - I_\perp}{I_\| + I_\perp} \qquad (1)$$

Here, P is the polarization, $I_\|$ is the intensity of luminescence polarized parallel to the polarization of the excitation light, and $I_\perp$ is the intensity of luminescence polarized perpendicular to the polarization of the excitation light. P generally varies from zero to one-half for randomly oriented molecules (and zero to one for aligned molecules). If there is little rotation between excitation and emission, $I_\|$ will be relatively large, $I_\perp$ will be relatively small, and P will be close to one-half. (P may be less than one-half even if there is no rotation; for example, P will be less than one-half if the absorption and emission dipoles are not parallel.) In contrast, if there is significant rotation between absorption and emission, $I_\|$ will be comparable to $I_\perp$, and P will be close to zero. Polarization often is reported in milli-P (mP) units (1000×P), which for randomly oriented molecules will range between 0 and 500, because P will range between zero and one-half.

Polarization also may be described using other equivalent quantities, such as anisotropy. The relationship between anisotropy and intensity is expressed by the following equation:

$$r = \frac{I_\| - I_\perp}{I_\| + 2I_\perp} \quad (2)$$

Here, r is the anisotropy. Polarization and anisotropy include the same information, although anisotropy may be more simply expressed for systems containing more than one luminophore. In the description and claims that follow, these terms may be used interchangeably, and a generic reference to one implies a generic reference to the other.

The relationship between polarization, luminescence lifetime, and rotational correlation time is expressed by the Perrin equation:

$$\left(\frac{1}{P} - \frac{1}{3}\right) = \left(\frac{1}{P_0} - \frac{1}{3}\right) \cdot \left(1 + \frac{\tau}{\tau_{rot}}\right) \quad (3)$$

Here, $P_0$ is the polarization in the absence of molecular motion (intrinsic polarization), $\tau$ is the luminescence lifetime (inverse decay rate), and $\tau_{rot}$ is the rotational correlation time (inverse rotational rate).

The Perrin equation shows that luminescence polarization assays are most sensitive when the luminescence lifetime and the rotational correlation time are similar. Rotational correlation time is proportional to molecular weight, increasing by about 1 nanosecond for each 2,400 Dalton increase in molecular weight (for a spherical molecule). For shorter lifetime luminophores, such as fluorescein, which has a luminescence lifetime of roughly 4 nanoseconds, luminescence polarization assays are most sensitive for molecular weights less than about 40,000 Daltons. For longer lifetime probes, such as Ru(bpy)$_2$dcbpy (ruthenium 2,2'-dibipyridyl 4,4'-dicarboxyl-2,2'-bipyridine), which has a lifetime of roughly 400 nanoseconds, luminescence polarization assays are most sensitive for molecular weights between about 70,000 Daltons and 4,000,000 Daltons.

c. Energy Transfer Modes

Energy transfer is the transfer of luminescence energy from a donor luminophore to an acceptor without emission by the donor. In energy transfer assays, a donor luminophore is excited from a ground state into an excited state by absorption of a photon. If the donor luminophore is sufficiently close to an acceptor, excited-state energy may be transferred from the donor to the acceptor, causing donor luminescence to decrease and acceptor luminescence to increase (if the acceptor is luminescent). The efficiency of this transfer is very sensitive to the separation R between donor and acceptor, decaying as $1/R^{-6}$. Energy transfer assays use energy transfer to monitor the proximity of donor and acceptor, which in turn may be used to monitor the presence or activity of an analyte, among others.

Energy transfer assays may focus on an increase in energy transfer as donor and acceptor are brought into proximity. These assays may be used to monitor binding, as between two molecules X and Y to form a complex X:Y. Here, colon (:) represents a noncovalent interaction. In these assays, one molecule is labeled with a donor D, and the other molecule is labeled with an acceptor A, such that the interaction between X and Y is not altered appreciably. Independently, D and A may be covalently attached to X and Y, or covalently attached to binding partners of X and Y.

Energy transfer assays also may focus on a decrease in energy transfer as donor and acceptor are separated. These assays may be used to monitor cleavage, as by hydrolytic digestion of doubly labeled substrates (peptides, nucleic acids). In one application, two portions of a polypeptide are labeled with D and A, so that cleavage of the polypeptide by a protease such as an endopeptidase will separate D and A and thereby reduce energy transfer. In another application, two portions of a nucleic acid are labeled with D and A, so that cleave by a nuclease such as a restriction enzyme will separate D and A and thereby reduce energy transfer.

Energy transfer between D and A may be monitored in various ways. For example, energy transfer may be monitored by observing an energy-transfer induced decrease in the emission intensity of D and increase in the emission intensity of A (if A is a luminophore). Energy transfer also may be monitored by observing an energy-transfer induced decrease in the lifetime of D and increase in the apparent lifetime of A.

In a preferred mode, a long-lifetime luminophore is used as a donor, and a short-lifetime luminophore is used as an acceptor. Suitable long-lifetime luminophores include metal-ligand complexes containing ruthenium, osmium, etc., and lanthanide chelates containing europium, terbium, etc. In time-gated assays, the donor is excited using a flash of light having a wavelength near the excitation maximum of D. Next, there is a brief wait, so that electronic transients and/or short-lifetime background luminescence can decay. Finally, donor and/or acceptor luminescence intensity is detected and integrated. In frequency-domain assays, the donor is excited using time-modulated light, and the phase and/or modulation of the donor and/or acceptor emission is monitored relative to the phase and/or modulation of the excitation light. In both assays, donor luminescence is reduced if there is energy transfer, and acceptor luminescence is observed only if there is energy transfer.

d. Steady-State and Time-Resolved Modes

Luminescence assays can be performed using steady-state and time-resolved modes. Apparatus 70, 90, and 160 may be used to conduct a variety of steady-state and time-resolved luminescence assays. Steady-state assays measure luminescence under constant illumination, typically using a continuous light source. Time-resolved assays measure luminescence as a function of time, typically using either a continuous light source, with its intensity appropriately modulated, or a time-varying light source. Time-resolved assays may be conducted in the time domain or in the frequency domain, both of which are functionally equivalent.

In a time-domain measurement, the time course of luminescence is monitored directly. Typically, a composition containing a luminescent analyte is illuminated using a narrow pulse of light, and the time dependence of the intensity of the resulting luminescence emission is observed, although other protocols also may be used. For a simple molecule, the luminescence commonly follows a single-exponential decay.

In a frequency-domain measurement, the time course of luminescence is monitored indirectly, in frequency space. Typically, the composition is illuminated using light whose intensity is modulated sinusoidally at a single modulation frequency f; although other protocols (such as transforming time-domain data into the frequency domain) also may be used. The intensity of the resulting luminescence emission is modulated at the same frequency as the excitation light. However, the emission will lag the excitation by a phase angle (phase) $\phi$, and the intensity of the emission will be demodulated relative to the intensity of the excitation by a demodulation factor (modulation) M.

Figure 4:
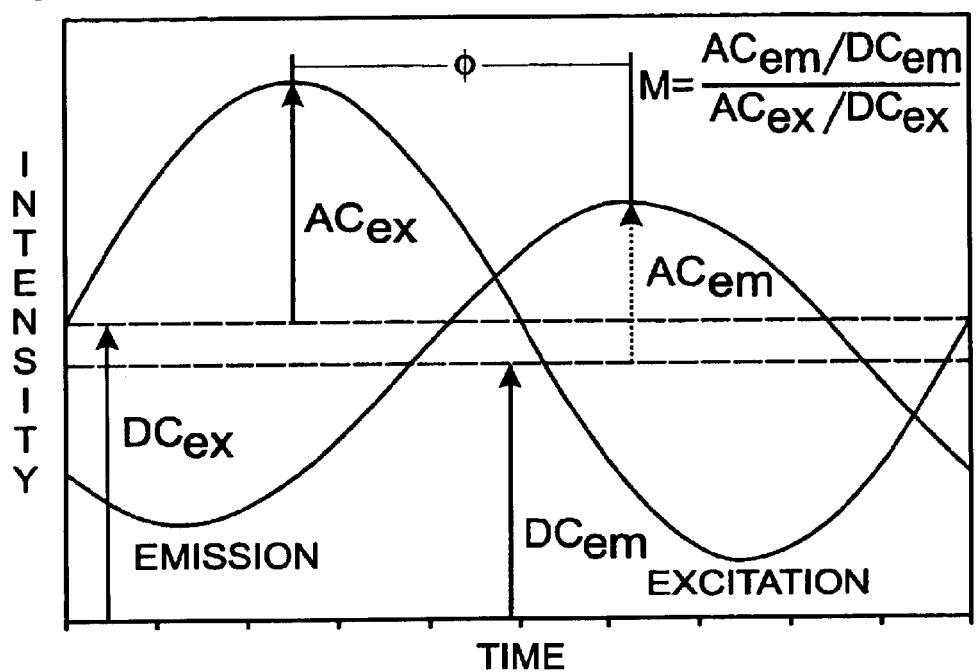
FIG. 4 is a schematic view of a frequency-domain time-resolved measurement, showing the definitions of phase angle (phase) $\phi$ and demodulation factor (modulation) M.

FIG. 4 shows the relationship between emission and excitation in a single-frequency frequency-domain experiment. The phase φ is the phase difference between the excitation and emission. The modulation M is the ratio of the AC amplitude to the DC offset for the emission, relative to the ratio of the AC amplitude to the DC offset for the excitation. The phase and modulation are related to the luminescence lifetime □ by the following equations:

$$\omega\tau = \tan(\phi) \quad (4)$$

$$\omega\tau = \sqrt{\frac{1}{M^2} - 1} \quad (5)$$

Here ω is the angular modulation frequency, which equals 2π times the modulation frequency. For maximum sensitivity, the angular modulation frequency should be roughly the inverse of the luminescence lifetime. Lifetimes of interest in high-throughput screening vary from less than 1 nanosecond to greater than 1 millisecond. Therefore, instruments for high-throughput screening should be able to handle modulation frequencies from less than about 200 Hz to greater than about 200 MHz.

B. Multi-Mode Instrument

A multi-mode instrument generally comprises any instrument capable of use in two or more optical measurement modes, such as absorption, luminescence, and/or scattering, and variants thereof. Such use may include analyzing a composition, including qualitative analysis (to determine the nature of the composition and/or its components) and/or quantitative analysis (to determine the amount, relative proportions, and/or activity of the composition and/or its components).

Figure 5:
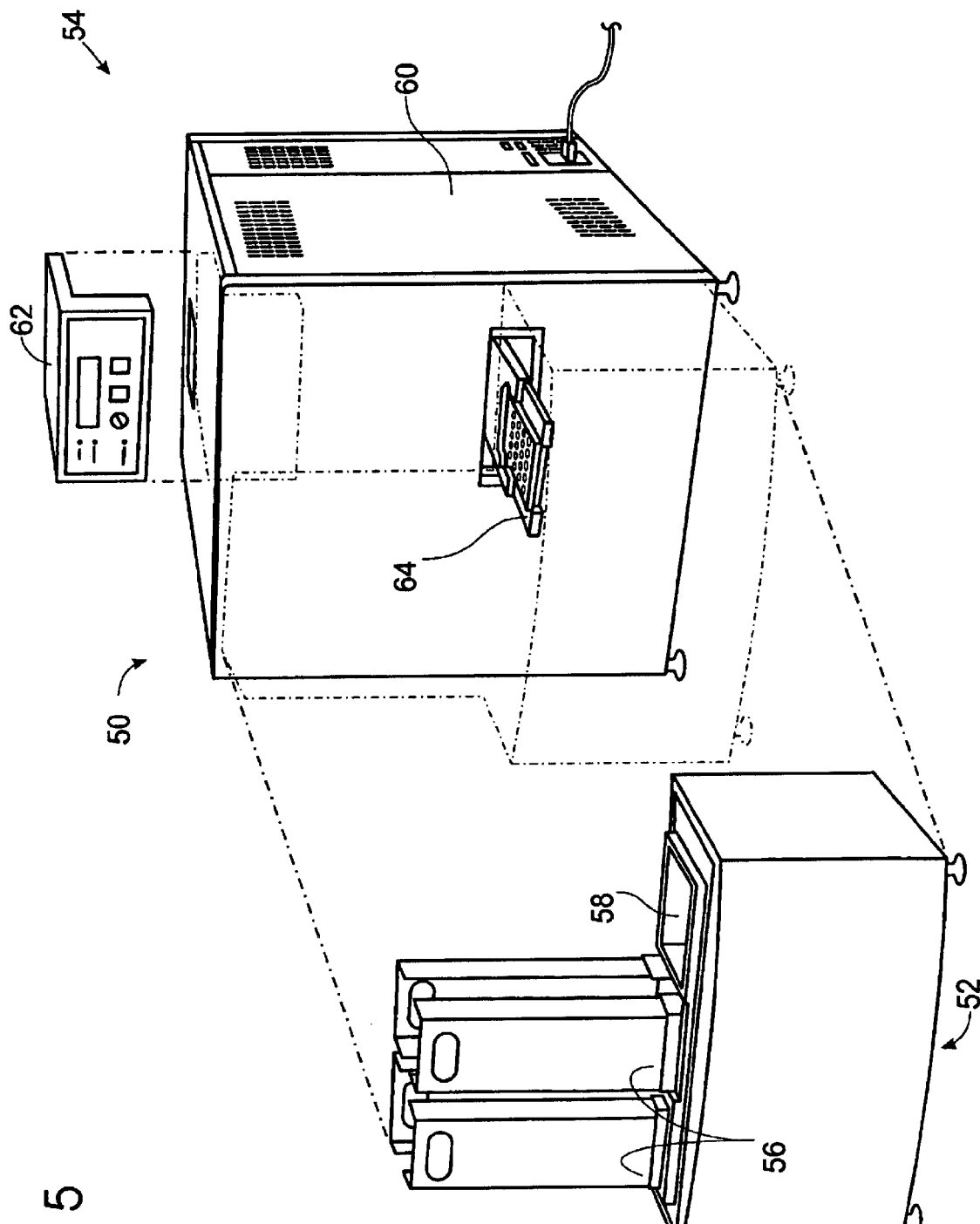
FIG. 5 is a partially exploded perspective view of a system for analyzing compositions in accordance with aspects of the invention, showing a transport module and an analysis module.

FIG. 5 shows a multimode instrument 50 having an optional transport module 52 for sample ingress and egress and an analysis module 54 for detecting and analyzing light in two or more optical modes. The transport module includes I/O sites 56, a transfer site 58, and mechanisms (not visible) for transporting sample holders between the I/O and transfer sites, as described above. The analysis module includes a housing 60, a moveable control unit 62, an optical system (not visible), and a transport mechanism 64. The housing may be used to enclose the analysis module, protecting the user and the components of the module. The control unit may be used to operate the module manually and/or robotically, as described in U.S. Pat. No. 6,025,985, which is incorporated herein by reference.

FIGS. 6–9 show details of the optical system 90 (and related components) of instrument 50. The optical system may include components for generating and/or detecting light, and for transmitting light to and/or from a composition. These components may include (1) a stage for supporting the composition, (2) one or more light sources for delivering light to the composition, (3) one or more detectors for receiving light transmitted from the composition and converting it to a signal, (4) first and second optical relay structures for relaying light between the light source, composition, and detector, and/or (5) a processor for analyzing the signal from the detector. Module components may be chosen to optimize speed, sensitivity, and/or dynamic range for one or more assay modes. For example, optical components with low intrinsic luminescence may be used to enhance sensitivity in luminescence assay modes by reducing background. Module components also may be shared by different assay modes, or dedicated to particular assay modes. For example, steady-state photoluminescence assay modes may use a continuous light source, time-resolved photoluminescence assay modes may use a time-varying light source, and chemiluminescence assay modes may not use a light source. Similarly, steady-state and time-resolved photoluminescence assay modes may both use a first detector, and chemiluminescence assay modes may use a second detector.

Optical system 90 includes (a) a photoluminescence optical system, and (b) a chemiluminescence optical system, as described below. Further aspects of the optical system are described in the following patent applications, which are incorporated herein by reference: U.S. patent application Ser. No. 09/160,533, filed Sep. 24, 1998; U.S. patent application Ser. No. 09/349,733, filed Jul. 8, 1999; PCT Patent Application Serial No. PCT/US99/16287, filed Jul. 26, 1999, published as WO 00/06990 on Feb. 10, 2000 (included herewith as Appendix E); and PCT Patent Application Serial No. PCT/US00/04543, filed Feb. 22, 2000, published as WO 00/50877 on Aug. 31, 2000 (included herewith as Appendix F).

1. Incident-Light-Based Optical System

Figure 6:
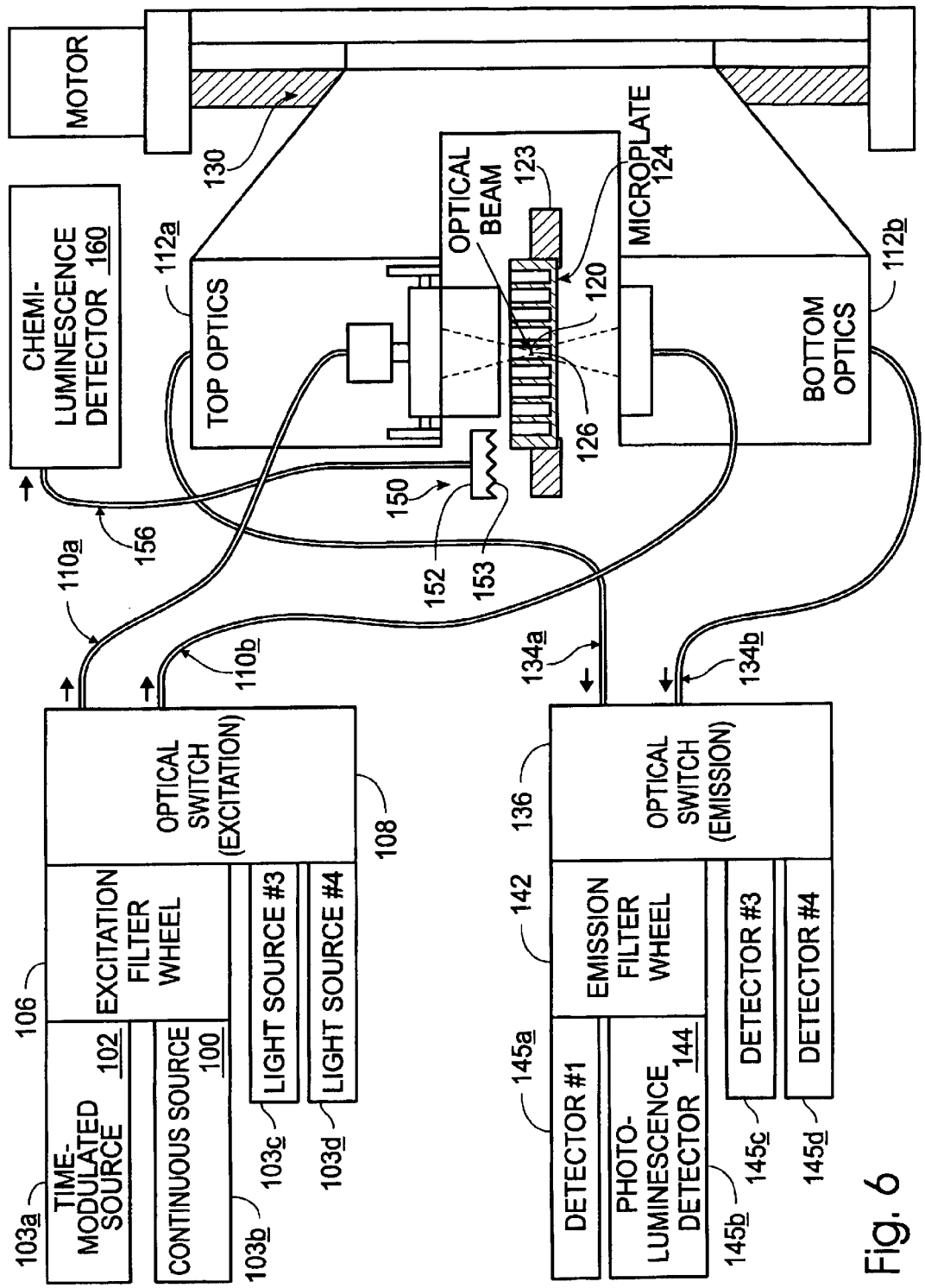
FIG. 6 is a schematic view of an optical system from the analysis module of FIG. 5.
Figure 7:
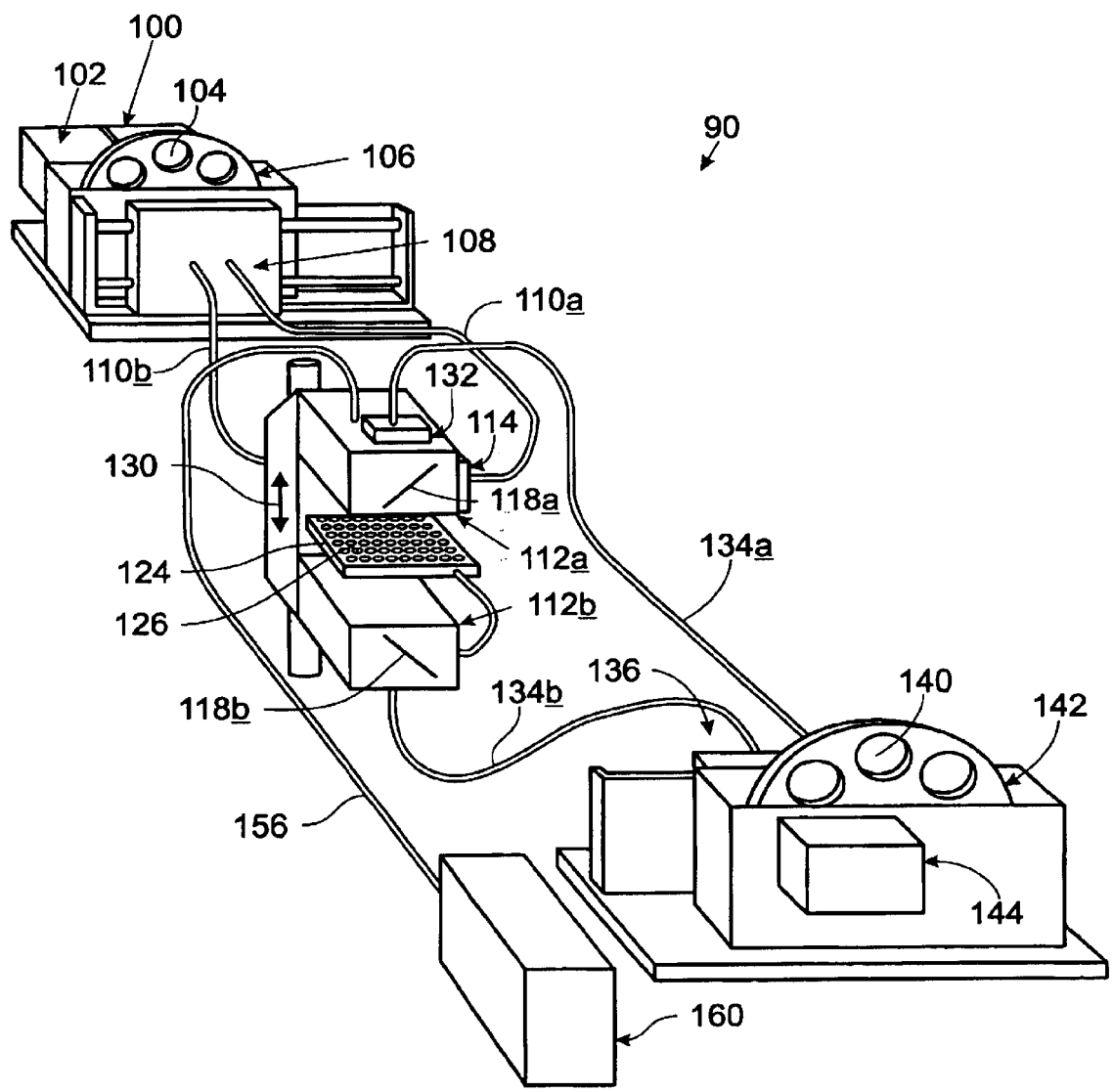
FIG. 7 is a partially schematic perspective view of the apparatus of FIG. 6.
Figure 8:
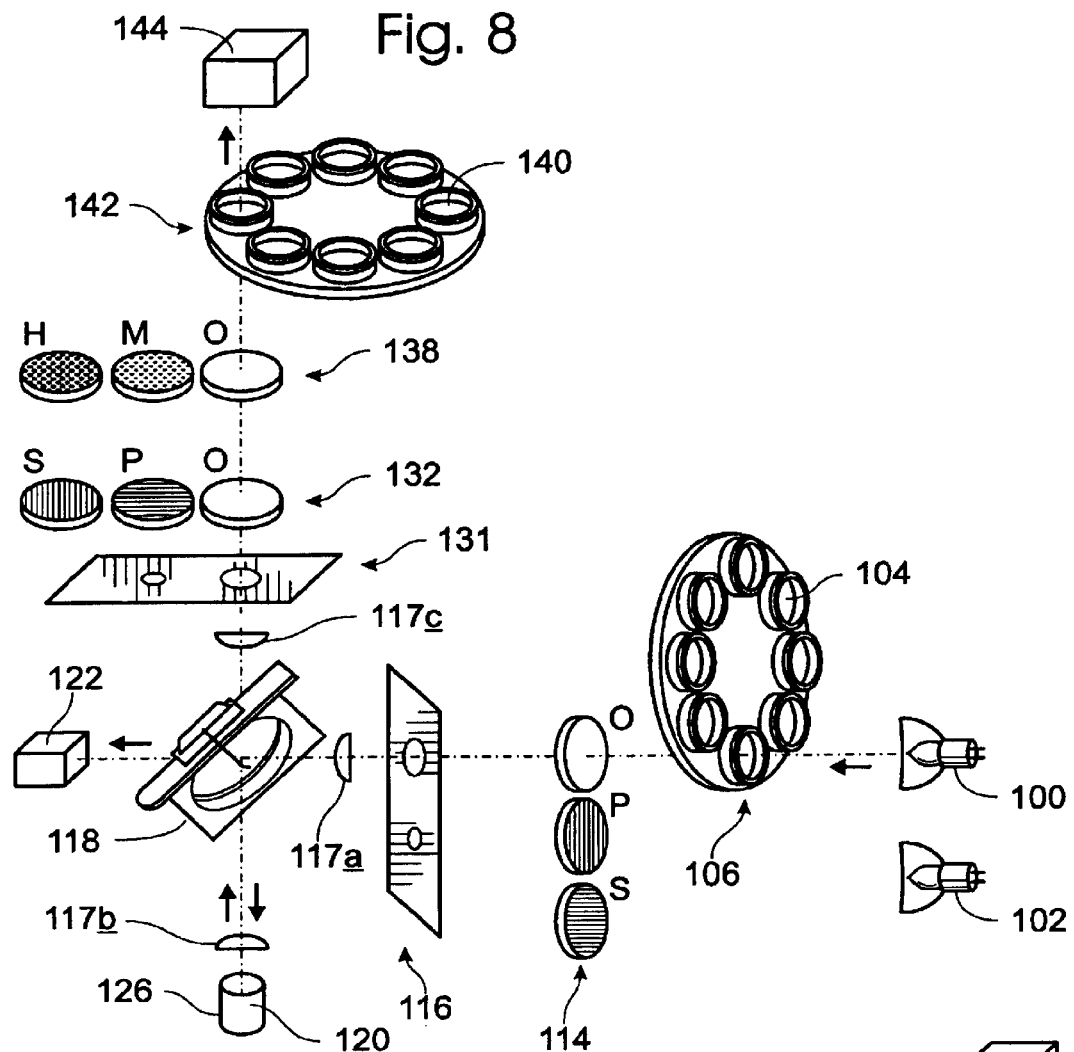
FIG. 8 is a schematic view of photoluminescence optical components from the apparatus of FIG. 6.

FIGS. 6–8 show the incident light-based (or photoluminescence) optical system of optical system 90. As configured here, optical system 90 includes a continuous light source 100 and a time-modulated light source 102. Optical system 90 includes light source slots 103a–d for four light sources, although other numbers of light source slots and light sources also could be provided Light source slots 103a–d function as housings that may surround at least a portion of each light source, providing some protection from radiation and explosion. The direction of light transmission through the incident light-based optical system is indicated by arrows.

Continuous source 100 provides light for absorbance, scattering, photoluminescence intensity, and steady-state photoluminescence polarization assay modes, among others. The continuous light source may include arc lamps, incandescent lamps, fluorescent lamps, electroluminescent devices, lasers, laser diodes, and light-emitting diodes (LEDs), among others. An exemplary continuous source is a high-intensity, high color temperature xenon arc lamp, such as a Model LX175F CERMAX xenon lamp from ILC Technology, Inc. Color temperature is the absolute temperature in Kelvin at which a blackbody radiator must be operated to have a chromaticity equal to that of the light source. A high color temperature lamp produces more light than a low color temperature lamp, and it may have a maximum output shifted toward or into visible wavelengths and ultraviolet wavelengths where many luminophores absorb. The preferred continuous source has a color temperature of 5600 Kelvin, greatly exceeding the color temperature of about 3000 Kelvin for a tungsten filament source. The preferred source provides more light per unit time than flash sources, averaged over the flash source duty cycle, increasing sensitivity and reducing read times. Optical system 90 may include a modulator mechanism configured to vary the intensity of light incident on the composition without varying the intensity of light produced by the light source. Further aspects of the continuous light source are described in U.S. patent application Ser. No. 09/349,733, filed Jul. 8, 1999, which is incorporated herein by reference.

Time-modulated source 102 provides light for time-resolved absorbance and/or photoluminescence assay modes, such as photoluminescence lifetime and time-resolved photoluminescence polarization assays. The time-modulated light source may include flash lamps, pulsed lasers, electronically modulated lasers and LEDs, and continuous lamps and other sources whose intensity can be modulated extrinsically using a Pockels cell, Kerr cell, or other mechanism. An exemplary time-modulated source includes a xenon flash lamp, such as a Model FX-1160 xenon flash lamp from EG&G Electro-Optics, as described in U.S. patent application Ser. No. 09/349,733, filed Jul. 8, 1999, which is incorporated herein by reference. Another exemplary time-modulated source includes a pulsed YAG laser in combination with an optical parametric oscillator (OPO), as described in U.S. Provisional Patent Application Ser. No. 60/244,012, filed Oct. 27, 2000, which is incorporated herein by reference. The exemplary sources produce a "flash" or "pulse" of light for a brief interval before signal detection and are especially well suited for time-domain measurements. Extrinsically modulated continuous light sources are especially well suited for frequency-domain measurements. An exemplary external modulator includes an amplitude modulator such as a chopper, as described in PCT Patent Application Serial No. PCT/US99/16287, filed Jul. 26, 1999. published as WO 00/06990 on Feb. 10, 2000 (included herewith as Appendix E), which is incorporated herein by reference.

In optical system 90, continuous source 100 and time-modulated source 102 produce multichromatic, unpolarized, and incoherent light. Continuous source 100 produces substantially continuous illumination, whereas time-modulated source 102 produces time-modulated illumination. Light from these light sources may be delivered to the composition without modification, or it may be filtered to alter its intensity, spectrum, polarization, or other properties.

Light produced by the light sources follows an excitation optical path to an examination site or measurement region. Such light may pass through one or more "spectral filters," which generally comprise any mechanism for altering the spectrum of light that is delivered to the composition. Spectrum refers to the wavelength composition of light A spectral filter may be used to convert white or multichromatic light, which includes light of many colors, into red, blue, green, or other substantially monochromatic light, which includes light of one or only a few colors. In optical system 90, spectrum is altered by an excitation interference filter 104, which preferentially transmits light of preselected wavelengths and preferentially absorbs light of other wavelengths. For convenience, excitation interference filters 104 may be housed in an excitation filter wheel 106, which allows the spectrum of excitation light to be changed by rotating a preselected filter into the optical path. Spectral filters also may separate light spatially by wavelength. Examples include gratings, monochromators, and prisms.

Spectral filters are not required for monochromatic ("single color") light sources, such as certain lasers, which output light of only a single wavelength. Therefore, excitation filter wheel 106 may be mounted in the optical path of some light source slots 103a,b, but not other light source slots 103c,d. Alternatively, the filter wheel may include a blank station that does not affect light passage.

Light next passes through an excitation optical shuttle (or switch) 108, which positions an excitation fiber optic cable 110a,b in front of the appropriate light source to deliver light to top or bottom optics heads 112a,b, respectively. Light is transmitted through a fiber optic cable much like water is transmitted through a garden hose. Fiber optic cables can be used easily to turn light around corners and to route light around opaque components of the apparatus. Moreover, fiber optic cables give the light a more uniform intensity profile. A preferred fiber optic cable is a fused silicon bundle, which has low autoluminescence. Despite these advantages, light also can be delivered to the optics heads using other mechanisms, such as mirrors.

Light arriving at the optics head may pass through one or more excitation "polarization filters," which generally comprise any mechanism for altering the polarization of light. Excitation polarization filters may be included with the top and/or bottom optics head. In optical system 90, polarization is altered by excitation polarizers 114, which are included only with top optics head 112a for top reading, however, such polarizers also can be included with bottom optics head 112b for bottom reading. Excitation polarization filters 114 may include an s-polarizer S that passes only s-polarized light, a p-polarizer P that passes only p-polarized light, and a blank O that passes substantially all light, where polarizations are measured relative to the beamsplitter or some other suitable reference. Excitation polarizers 114 also may include a standard or ferro-electric liquid crystal display (LCD) polarization switching system. Such a system may be faster than a mechanical switcher. Excitation polarizers 114 also may include a continuous mode LCD polarization rotator with synchronous detection to increase the signal-to-noise ratio in polarization assay modes. Excitation polarizers 114 may be incorporated as an inherent component in some light sources, such as certain lasers, that intrinsically produce polarized light. Further aspects of the polarization filters and their use in polarization assay are described in the following U.S. Patent Applications, which are incorporated herein by reference: Ser. No. 09/349,733, filed Jul. 8, 1999; and Ser. No. 09/629,599, filed Jul. 31, 2000.

Light at one or both optics head s also may pass through an excitation "confocal optics element," which generally comprises any mechanism for focusing light into a "sensed volume." In optical system 90, the confocal optics element includes a set of lenses 117a–c and an excitation aperture 116 placed in an image plane conjugate to the sensed volume, as shown in FIG. 8. Aperture 116 may be implemented directly, as an aperture, or indirectly, as the end of a fiber optic cable. Preferred apertures have diameters of 1 mm and 1.5 mm. Lenses 117a,b project an image of aperture 116 onto the composition, so that only a preselected or sensed volume of the composition is illuminated. The area of illumination will have a diameter corresponding to the diameter of the excitation aperture.

Light traveling through the optics head is directed onto a beamsplitter 118, which reflects light toward a composition 120 and transmits light toward a light monitor 122. The reflected light passes through lens 117b, which is operatively positioned between beamsplitter 118 and composition 120.

Beamsplitter 118 is used to direct excitation or incident light toward the composition and light monitor, and to direct light leaving the composition toward the detector. The beamsplitter is changeable, so that it may be optimized for different assay modes or compositions. In some embodiments, switching between beamsplitters may be performed manually, whereas in other embodiments, such switching may be performed automatically. Automatic switching may be performed based on direct operator command, or based on an analysis of the composition by the instrument. If a large number or variety of photoactive molecules are to be studied, the beamsplitter must be able to accommodate light of many wavelengths; in this case, a "50:50" beamsplitter that reflects half and transmits half of the incident light independent of wavelength is optimal. Such a beamsplitter can be used with many types of molecules, while still delivering considerable excitation light onto the composition, and while still transmitting considerable light leaving the composition to the detector. If one or a few related photoactive molecules are to be studied, the beamsplitter needs only to be able to accommodate light at a limited number of wavelengths; in this case, a "dichroic" or "multidichroic" beamsplitter is optimal. Such a beamsplitter can be designed with cutoff wavelengths for the appropriate sets of molecules and will reflect most or substantially all of the excitation and background light, while transmitting most or substantially all of the emission light in the case of luminescence. This is possible because the beamsplitter may have a reflectivity and transmissivity that varies with wavelength.

The beamsplitter more generally comprises any optical device for dividing a beam of light into two or more separate beams. A simple beamsplitter (such as a 50:50 beamsplitter) may include a very thin sheet of glass inserted in the beam at an angle, so that a portion of the beam is transmitted in a first direction and a portion of the beam is reflected in a different second direction. A more sophisticated beamsplitter (such as a dichroic or multi-dichroic beamsplitter) may include other prismatic materials, such as fused silica or quartz, and may be coated with a metallic or dielectric layer having the desired transmission and reflection properties, including dichroic and multi-dichroic transmission and reflection properties. In some beamsplitters, two right-angle prisms are cemented together at their hypotenuse faces, and a suitable coating is included on one of the cemented faces. Further aspects of the beamsplitter are described in PCT Patent Application Serial No. PCT/US00/06841, filed Mar. 15, 2000. published as WO 00/55372 on Sep. 21, 2000 (Included herewith as Appendix G), which is incorporated herein by reference.

Light monitor 122 is used to correct for fluctuations in the intensity of light provided by the light sources. Such corrections may be performed by reporting detected intensities as a ratio over corresponding times of the luminescence intensity measured by the detector to the excitation light intensity measured by the light monitor. The light monitor also can be programmed to alert the user if the light source fails. A preferred light monitor is a silicon photodiode with a quartz window for low autoluminescence.

The composition (or sample) may be held in a sample holder supported by a stage 123. The composition can include compounds, mixtures, surfaces, solutions, emulsions, suspensions, cell cultures, fermentation cultures, cells, tissues, secretions, and/or derivatives and/or extracts thereof. Analysis of the composition may involve measuring the presence, concentration, or physical properties (including interactions) of a photoactive analyte in such a composition. Composition may refer to the contents of a single microplate well, or several microplate wells, depending on the assay. In some embodiments, such as a portable apparatus, the stage may be intrinsic to the instrument.

The sample holder 124 generally comprises any mechanism for supporting a composition, and particularly a plurality of compositions, for analysis. Suitable sample holders include microplates, PCR plates, biochips, hybridization chambers, chromatography plates, microscope slides, and gel slabs, among others. These sample holders may include discrete sample sites 126, where distinct samples are separated using any suitable separation mechanism, including walls (microplates and PCR plates), adhesion (biochips), and/or diffusive barriers (gel slabs), among others. These sample holders also may include continuous sample sites, where "samples" are created by separately analyzing different regions of the sample holder. Preferred microplates are described in the following U.S. Patent Applications, which are incorporated herein by reference: Ser. No. 08/840,553, filed Apr. 14, 1997; Ser. No. 09/156,318, filed Sep. 18, 1998; and Ser. No. 09/478,819, filed Jan. 5, 2000. These microplates may include 96, 384, 1536, or other numbers of wells. These microplates also may include wells having elevated bottoms, small ($\leq 50$ $\mu L$) volumes, and/or frustoconical shapes capable of matching a sensed volume. A "standard" microplate includes 96 cylindrical sample wells disposed in a 8×12 rectangular array on 9 millimeter centers. Preferred PCR plates may include the same (or a similar) footprint, well spacing, and well shape as the preferred microplates, while possessing stiffness adequate for automated handling and thermal stability adequate for PCR. Preferred biochips are described in Bob Sinclair, *Everything's Great When It Sits on a Chip: A Bright Future for DNA Arrays,* 13 The Scientist, May 24, 1999, at 18. Preferred hybridization chambers are described in PCT Patent Application Serial No. PCT/US99/16453, filed Jul. 21, 1999, published as WO 00/05336 on Feb. 3, 2000 (included herewith as Appendix A), which is incorporated herein by reference.

The sensed volume may have an hourglass shape, with a cone angle of about 25° and a minimum diameter ranging between 0.1 mm and 2.0 mm. For 96-well and 384-well microplates, a preferred minimum diameter is about 1.5 mm. For 1536-well microplates, a preferred minimum diameter is about 1.0 mm. The size and shape of the sample holder. may be matched to the size and shape of the sensed volume, as described in the following U.S. Patent Applications, which are incorporated herein by reference: Ser. No. 09/062,472, filed Apr. 17, 1998; and Ser. No. 09/478,81, filed Jan. 5, 2000.

The position of the sensed volume can be moved precisely within the composition to optimize the signal-to-noise and signal-to-background ratios. For example, the sensed volume may be moved away from walls in the sample holder to optimize signal-to-noise and signal-to-background ratios, reducing spurious signals that might arise from luminophores bound to the walls and thereby immobilized. In optical system 90, position in the X,Y-plane perpendicular to the optical path is controlled by moving the stage supporting the composition, whereas position along the Z-axis parallel to the optical path is controlled by moving the optics head s using a Z-axis adjustment mechanism 130, as shown in FIGS. 5 and 6. However, any mechanism for bringing the sensed volume into register or alignment with the appropriate portion of the composition also may be employed. For example, the optics head also may be scanned in the X,Y-plane, as described in the following patent applications, which are incorporated herein by reference: U.S. Provisional Patent Application Ser. No. 60/142,721, filed Jul. 7, 1999; and PCT Patent Application Serial No. US00/18547, filed Jul. 7, 2000. published as WO 01/04608 on Jan. 18, 2001 (included herewith as Appendix C).

The combination of top and bottom optics permits assays to combine: (1) top illumination and top detection, or (2) top illumination and bottom detection, or (3) bottom illumination and top detection, or (4) bottom illumination and bottom detection. Same-side illumination and detection, (1) and (4), is referred to as "epi" and may be used for luminescence, epi-absorption, and/or scattering assays, among others. Opposite-side illumination and detection, (2) and (3), is referred to as "trans" and may be used for trans-absorption assays, among others. In optical system 90, epi modes are supported, so the excitation and emission light travel the same path in the optics head, albeit in opposite or anti-parallel directions. However, trans modes also can be used with additional sensors, as described below. In optical system 90, top and bottom optics head s move together and share a common focal plane. However, in other embodiments, top and bottom optics head s may move independently, so that each can focus independently on the same or different sample planes. Further aspects of top and bottom optics are described in the following patents and patent applications, which are incorporated herein by reference: U.S. Pat. No. 6,097,025, issued Aug. 1, 2000; and PCT Patent Application Serial No. PCT/US99/16621, filed Jul. 23, 1999. published as WO 00/06991 on Feb. 10, 2000 (included herewith as Appendix D).

Generally, top optics can be used with any sample holder having an open top, whereas bottom optics can be used only with sample holders having optically transparent bottoms, such as glass or thin plastic bottoms. Clear bottom sample holders are particularly suited for measurements involving analytes and/or cells that accumulate on the bottom of the holder.

Light may be transmitted by the composition in multiple directions. A portion of the transmitted light will follow an emission pathway to a detector. Transmitted light passes through lens 117c and may pass through an emission aperture 131 and/or an emission polarizer 132. In optical system 90, the emission aperture is placed in an image plane conjugate to the sensed volume and transmits light substantially exclusively from this sensed volume. In optical system 90, the emission apertures in the top and bottom optical system s are the same size as the associated excitation apertures, although other sizes also may be used. The emission polarizers are included only with top optics head 112a. The emission aperture and emission polarizer are substantially similar to their excitation counterparts. Emission polarizer 132 may be included in detectors that intrinsically detect the polarization of light.

Excitation polarizers 114 and emission polarizers 132 may be used together in nonpolarization assays to reject certain background signals. Luminescence from the sample holder and from luminescent molecules adhered to the sample holder is expected to be polarized, because the rotational mobility of these molecules should be hindered. Such polarized background signals can be eliminated by "crossing" the excitation and emission polarizers, that is, setting the angle between their transmission axes at 90°. As described above, such polarized background signals also can be reduced by moving the sensed volume away from walls of the sample holder. To increase signal level, beamsplitter 118 should be optimized for reflection of one polarization and transmission of the other polarization. This method will work best where the luminescent molecules of interest emit relatively unpolarized light, as will be true for small luminescent molecules in solution.

Transmitted light next passes through an emission fiber optic cable 134a,b to an emission optical shuttle (or switch) 136. This shuttle positions the appropriate emission fiber optic cable in front of the appropriate detector. In optical system 90, these components art substantially similar to their excitation counterparts, although other mechanisms also could be employed.

Light exiting the fiber optic cable next may pass through one or more emission "intensity filters," which generally comprise any mechanism for reducing the intensity of light. Intensity refers to the amount of light per unit area per unit time. In optical system 90, intensity is altered by emission neutral density filters 138, which absorb light substantially independent of its wavelength, dissipating the absorbed energy as heat. Emission neutral density filters 138 may include a high-density filter H that absorbs most incident light, a medium-density filter M that absorbs somewhat less incident light, and a blank O that absorbs substantially no incident light. These filters may be changed manually, or they may be changed automatically, for example, by using a filter wheel. Intensity filters also may divert a portion of the light away from the composition without absorption. Examples include beam splitters, which transmit some light along one path and reflect other light along another path, and diffractive beam splitters (e.g., acousto-optic modulators), which deflect light along different paths through diffraction. Examples also include hot mirrors or windows that transmit light of some wavelengths and absorb light of other wavelengths.

Light next may pass through an emission spectral filter 140, which may be housed in an emission filter wheel 142. In optical system 90, these components are substantially similar to their excitation counterparts, although other mechanisms also could be employed. Emission spectral filters block stray excitation light in photoluminescence assay modes, which may enter the emission path through various mechanisms, including reflection and scattering. If unblocked, such stray excitation light could be detected and misidentified as photoluminescence, decreasing the signal-to-background ratio. Emission spectral filters can separate photoluminescence from excitation light because photoluminescence has longer wavelengths than the associated excitation light. Luminescence typically has wavelengths between 200 and 2000 nanometers.

The relative positions of the spectral, intensity, polarization, and other filters presented in this description may be varied without departing from the spirit of the invention. For example, filters used here in only one optical path, such as intensity filters, also may be used in other optical paths. In addition, filters used here in only top or bottom optics, such as polarization filters, may also be used in the other of top or bottom optics or in both top and bottom optics. The optimal positions and combinations of filters for a particular experiment will depend on the assay mode and the composition, among other factors.

Light last passes to a detector, which is used in absorbance, scattering and photoluminescence assays, among others. In optical system 90, there is one detector 144, which detects light from all modes. A preferred detector is a photomultiplier tube (PMT). Optical system 90 includes detector slots 145–d for four detectors, although other numbers of detector slots and detectors also could be provided.

More generally, detectors comprise any mechanism capable of converting energy from detected light into signals that may be processed by the apparatus, and by the processor in particular. Suitable detectors include photomultiplier tubes, photodiodes, avalanche photodiodes, charge-coupled devices (CCDs), and intensified CCDs, among others. Depending on the detector, light source, and assay mode, such detectors may be used in a variety of detection modes. These detection modes include (1) discrete (e.g., photon-counting) modes, (2) analog (e.g., current-integration) modes, and/or (3) imaging modes, among others, as described in PCT Patent Application Serial No. PCT/US99/03678, published as WO 99/42817 on Aug. 26, 1999 (included herewith as Appendix H).

2. Chemiluminescence Optical System

Figure 9:
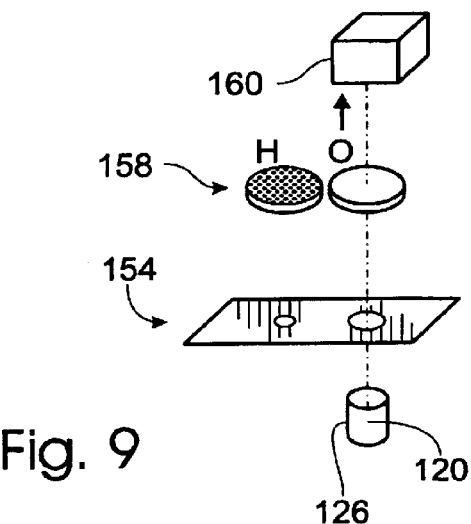
FIG. 9 is a schematic view of chemiluminescence optical components from the apparatus of FIG. 6.

FIGS. 6, 7, and 9 show the chemiluminescence optical system of optical system 90. Because chemiluminescence follows a chemical event rather than the absorption of light, the chemiluminecsence optical system does not require a light source or other excitation optical components. Instead, the chemiluminescence optical system requires only selected emission optical components. In optical system 90, a separate lensless chemiluminescence optical system is employed, which is optimized for maximum sensitivity in the detection of chemiluminescence.

Generally, components of the chemiluminescence optical system perform the same functions and are subject to the same caveats and alternatives as their counterparts in the incident light-based optical system. The chemiluminescence optical system also can be used for other assay modes that do not require illumination, such as eectrochemiluminescence.

The chemiluminescence optical path begins with a chemiluminescent composition 120 held in a sample holder 126. The composition and sample holder are analogous to those used in photoluminescence assays; however, analysis of the composition involves measuring the intensity of light generated by a chemilumineseence reaction within the composition rather than by light-induced photoluminescence. A familiar example of chemiluminescence is the glow of the firefly.

Chemiluminescence light typically is transmitted from the composition in all directions, although most will be absorbed or reflected by the walls of the sample holder. A portion of the light transmitted through the top of the well is collected using a chemiluminescence head 150, as shown in FIG. 6, and will follow a chemiluminescence optical pathway to a detector. The direction of light transmission through the chemiluminescence optical system is indicated by arrows.

The cheniluminescence head includes a nonconfocal mechanism for transmitting light from a sensed volume within the composition. Detecting from a sensed volume reduces contributions to the chemiluminescence signal resulting from "cross talk," which is pickup from neighboring wells. The nonconfocal mechanism includes a chemiluminescence baffle 152, which includes rugosities 153 that absorb or reflect light from other wells. The nonconfocal mechanism also includes a chemiluminescence aperture 154 that further confines detection to a sensed volume.

Light next passes through a chemiluminescence fiber optic cable 156, which may be replaced by any suitable mechanism for directing light from the composition toward the detector. Fiber optic cable 156 is analogous to excitation and emission fiber optic cables 110*a,b* and 134*a,b* in the photoluminescence optical system. Fiber optic cable 156 may include a transparent, open-ended lumen that may be filled with fluid. This lumen would allow the fiber optic to be used both to transmit luminescence from a microplate well and to dispense fluids into the microplate well. The effect of such a lumen on the optical properties of the fiber optic could be minimized by employing transparent fluids having optical indices matched to the optical index of the fiber optic.

Light next passes through one or more chemiluminescence intensity filters, which generally comprise any mechanism for reducing the intensity of light. In optical system 90, intensity is altered by chemiluminescence neutral density filters 158. Light also may pass through other filters, if desired.

Light last passes to a detector, which converts light into signals that may be processed by the apparatus. In optical system 90, there is one chemiluminescence detector 160. This detector may be selected to optimize detection of blue/green light, which is the type most often produced in chemiluminescence. A preferred detection is a photomultiplier tube, selected for high quantum efficiency and low dark count at chemiluminescence wavelengths (400–500 nanometers).

3. Selected Examples

Selected aspects of the invention also may be described as recited in the following numbered paragraphs:

1. A method of performing optical analysis on a composition, comprising positioning the composition at an examination site in a multi-mode instrument, detecting light transmitted from the composition using the multi-mode installment in a first optical measurement mode, computing a first quantity related to a property of the composition using the light detected in the first optical measurement mode, comparing the quantity to a preselectable criterion, and if the quantity matches the preselectable criterion, detecting light transmitted from the composition using the multi-mode instrument in a second optical measurement mode, where the second mode is different than the first mode.

2. The method of paragraph 1, where the multi-mode instrument is capable of detecting light in at least two optical measurement modes selected from the group consisting of absorption, luminescence, and scattering.

3. The method of paragraph 1, further comprising automatically switching the multi-mode instrument from the first optical measurement mode to the second optical measurement mode.

4. The method of paragraph 1, where one or both of the steps of detecting light using the first and second modes are performed simultaneously on a plurality of compositions for optical analysis of the plurality of compositions.

5. The method of paragraph 1, where one or both of the steps of detecting light using the first and second modes are performed successively on a plurality of compositions for optical analysis of the plurality of compositions.

6. The method of paragraph 1, where the step of detecting light using the first mode is performed successively on a plurality of compositions for optical analysis of the plurality of compositions, and then the step of detecting light using the second mode is performed on some or all of the plurality of compositions.

7. The method of paragraph 1, further comprising computing a second quantity using the light detected in the second optical measurement mode, and assessing the presence or effects of a potential source of error on the first quantity using the second quantity.

8. The method of paragraph 7, where the first optical measurement mode is luminescence, and where the second optical measurement mode is selected from the group consisting of absorption and scattering.

9. The method of paragraph 1, where the first optical measurement mode is luminescence.

10. The method of paragraph 9, where the second optical measurement mode is scattering.

11. The method of paragraph 10, further comprising assessing the presence or effects of turbidity on the first quantity using the light detected in the second optical measurement mode.

12. The method of paragraph 9, where the second optical measurement mode is absorption.

13. The method of paragraph 12, further comprising assessing the presence or effects of color quenching and/or a contaminant on the first quantity using the light detected in the second optical measurement mode.

14. The method of paragraph 1, where the first quantity is selected from the group consisting of absorbance, chemiluminescence intensity, photoluminescence intensity, photoluminescence energy transfer, photoluminescence lifetime, and photoluminescence polarization.

15. The method of paragraph 1, where the property of the composition is the presence or activity of a component of the composition.

16. The method of paragraph 1, further comprising detecting light transmitted from the composition using the multi-mode instrument in a third optical measurement mode, where the third mode is different than the first and second modes.

17. The method of paragraph 1, further comprising repeating the step of detecting light using the first mode based on an outcome of the step of detecting light using the second mode.

Although the invention has been disclosed in its preferred forms, the specific embodiments thereof as disclosed and illustrated herein are not to be considered in a limiting sense, because numerous variations are possible. For example, an absorbance assay may be combined with a SPA assay or a luminescence assay to look for strong absorbance at any wavelength relative to a cohort group to detect false positives due to quenching. Applicants regard the subject matter of their invention to include all novel and non-obvious combinations and subcombinations of the various elements, features, functions, and/or properties disclosed herein. No single feature, fiction, element, or properly of the disclosed embodiments is essential. The following claims define certain combinations and subcombinations of features, functions, elements, and/or properties that are regarded as novel and nonobvious. Other combinations and subcombinations may be claimed through amendment of the present claims or presentation of new claims in this or a related application. Such claims, whether they are broader, narrower, or equal in scope to the original claims, also are regarded as included within the subject matter of applicant's invention.

We claim:

1. A method of performing optical analysis on a plurality of compositions, comprising:
    positioning the plurality of compositions automatically at an examination site in a multi-mode instrument, the compositions being disposed in a two-dimensional array;
    detecting light transmitted from the compositions using the multi-mode instrument in a first optical measurement mode;
    detecting light transmitted from one or more of the compositions using the multi-mode instrument in a second optical measurement mode, where the second mode is different than the first mode; and
    computing a first quantity related to a property of at least one of the compositions using the light detected in at least one of the optical measurement modes.

2. The method of claim 1, where the multi-mode instrument is capable of detecting light in at least two optical measurement modes selected from the group consisting of absorption, luminescence, and scattering.

3. The method of claim 1, where the steps of detecting light using the first and second optical modes are performed sequentially on at least one of the one or more compositions.

4. The method of claim 3, further comprising automatically switching the multi-mode instrument from the first optical measurement mode to the second optical measurement mode.

5. The method of claim 1, where the steps of detecting light using the first and second optical modes are performed simultaneously on at least one of the one or more compositions.

6. The method of claim 1, where the step of detecting light using the first mode is performed simultaneously on the plurality of compositions for optical analysis of the plurality of compositions.

7. The method of claim 1, where the step of detecting light using the first mode is performed successively on the plurality of compositions for optical analysis of the plurality of compositions.

8. The method of claim 1, where the step of detecting light using the second mode is performed after the step of detecting light using the first mode.

9. The method of claim 1, the first quantity being computed using the light detected in the first optical measurement mode, further comprising:
    computing a second quantity using the light detected in the second optical measurement mode; and
    assessing the presence or effects of a potential source of error on the first quantity using the second quantity.

10. The method of claim 9, where the first optical measurement mode is luminescence, and where the second optical measurement mode is selected from the group consisting of absorption and scattering.

11. The method of claim 1, where the first optical measurement mode is luminescence.

12. The method of claim 11, where the second optical measurement mode is scattering.

13. The method of claim 12, further comprising assessing the presence or effects of turbidity on the first quantity using the light detected in the second optical measurement mode.

14. The method of claim 11, where the second optical measurement mode is absorption.

15. The method of claim 14, further comprising assessing the presence or effects of color quenching and/or a contaminant on the first quantity using the light detected in the second optical measurement mode.

16. The method of claim 1, where the first quantity is selected from the group consisting of absorbance, chemiluminescence intensity, photoluminescence intensity, photoluminescence energy transfer, photoluminescence lifetime, and photoluminescence polarization.

17. The method of claim 1, where the property of the at least one composition is the presence or activity of a component of the at least one composition.

18. The method of claim 1, further comprising detecting light transmitted from at least one of the compositions using the multi-mode instrument in a third optical measurement mode, where the third mode is different than the first and second modes.

19. The method of claim 1, further comprising determining to perform the step of detecting light using the second mode based on an outcome of the step of detecting light using the first mode.

20. The method of claim 1, further comprising repeating the step of detecting light using the first mode based on an outcome of the step of detecting light using the second mode.

21. The method of claim 1, where the two-dimensional array is defined by a microplate.

22. The method of claim 1, where the two-dimensional array is defined by a biochip.

23. A method of performing optical analysis on a plurality of compositions, comprising:
    positioning the plurality of compositions automatically at an examination site in a multi-mode instrument, the compositions being disposed in a two-dimensional array;
    detecting light transmitted from the compositions using the multi-mode instrument in a first optical measurement mode;

computing a first quantity related to a property of one or more of the compositions using the light detected in the first optical measurement mode;

comparing the quantity to a preselectable criterion; and if the quantity matches the preselectable criterion, detecting light transmitted from the one or more compositions using the multi-mode instrument in a second optical measurement mode, where the second mode is different than the first mode.

24. The method of claim 23, where the preselectable criterion is a set of acceptable values for the first quantity, so that light transmitted from the one or more compositions is detected using the second mode if the first quantity is an acceptable value.

25. The method of claim 23, where the preselectable criterion is a set of unacceptable values for the first quantity, so that light transmitted from the one or more compositions is detected using the second mode if the first quantity is an unacceptable value.

26. The method of claim 23, further comprising:

computing a second quantity related to a property of the one or more compositions using the light detected in the second optical measurement mode; and assessing the presence or effects of a potential source of error on the first quantity using the second quantity.

27. A system for performing optical analysis on a plurality of compositions, comprising:

a multi-mode instrument configured to detect light automatically from the plurality of compositions in a first optical measurement mode and from one or more of the compositions in a second optical measurement mode, where the first mode is different than the second mode, and where the plurality of compositions are disposed in a two-dimensional array; and a processor that uses measurements from more than one optical measurement mode to compute a quantity relating to a characteristic of the one or more compositions.

28. The system of claim 27, where the multi-mode instrument indudes a light source, a detector, an examination site, and an optical relay structure positioned to transmit light from the light source to a composition at the examination site, and from the composition to the detector.

* * * * *